(12) United States Patent
Wu et al.

(10) Patent No.: US 9,056,163 B2
(45) Date of Patent: Jun. 16, 2015

(54) SAFETY DRUG DELIVERY SYSTEM

(75) Inventors: Yongxian Wu, Wayne, NJ (US); Yun Jin, Morristown, NJ (US); Mitali Aon, Princeton Junction, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 12/711,805

(22) Filed: Feb. 24, 2010

(65) Prior Publication Data
US 2011/0208160 A1 Aug. 25, 2011

(51) Int. Cl.
*A61M 39/00* (2006.01)
*A61M 5/165* (2006.01)
*A61M 39/26* (2006.01)

(52) U.S. Cl.
CPC .............. *A61M 5/165* (2013.01); *A61M 39/26* (2013.01); *A61M 2005/1652* (2013.01)

(58) Field of Classification Search
CPC ... A61M 39/26; A61M 39/24; A61M 25/007; A61M 39/045; A61M 2039/267; A61M 39/10; A61M 2039/1094
USPC ......... 604/511, 512, 513, 523, 533, 534, 535, 604/536, 537, 538, 539, 190, 406; 251/149.7
See application file for complete search history.

(56) References Cited

U.S. PATENT DOCUMENTS

| 3,557,778 A | 1/1971 | Hughes |
| 3,570,484 A | 3/1971 | Steer |
| 3,815,754 A | 6/1974 | Rosenberg |
| 4,143,853 A | 3/1979 | Abramson |
| 4,336,036 A * | 6/1982 | Leeke et al. .................... 96/219 |
| 4,387,879 A | 6/1983 | Tauschinski |
| 4,485,014 A | 11/1984 | Gilroy et al. |
| 4,683,916 A | 8/1987 | Raines |
| 4,740,205 A | 4/1988 | Seltzer et al. |
| 4,838,875 A | 6/1989 | Somor |

(Continued)

FOREIGN PATENT DOCUMENTS

| CN | 2484967 | 4/2002 |
| CN | 2724746 | 9/2005 |

(Continued)

OTHER PUBLICATIONS

Stabile, M. et al., "Medical Administration in Anesthesia", *Anesthesia Patient Safety Foundation Newsletter*, vol. 22, No. 3, (2007), 6 pgs.

(Continued)

*Primary Examiner* — Aarti B Berdichevsky
(74) *Attorney, Agent, or Firm* — Servilla Whitney LLC

(57) ABSTRACT

Drug delivery systems are provided that include an actuator assembly permanently attached to a filter for connection of a container containing medications such as epidural anesthesia, to a delivery site. In one or more embodiments, the actuator assembly includes a projection with an opening extending from a distal end of the actuator assembly in a proximal direction and the filter includes an inlet and an outlet in fluid communication with the opening. The filter includes a housing including two plates joined together or a cylindrical body defining a cavity containing filter materials. A conduit may be attached to the outlet of the filter to allow connection of the drug delivery systems described to a delivery site, such as a catheter. Methods of administering a medication to a delivery site are also provided.

16 Claims, 19 Drawing Sheets

(56) References Cited

U.S. PATENT DOCUMENTS

| | | | |
|---|---|---|---|
| 5,069,225 | A | 12/1991 | Okamura |
| 5,100,394 | A | 3/1992 | Dudar et al. |
| 5,190,067 | A | 3/1993 | Paradis et al. |
| 5,349,984 | A | 9/1994 | Weinheimer et al. |
| 5,376,073 | A | 12/1994 | Graves et al. |
| 5,390,898 | A | 2/1995 | Smedley et al. |
| 5,437,648 | A | 8/1995 | Graves et al. |
| 5,437,650 | A | 8/1995 | Larkin et al. |
| 5,465,938 | A | 11/1995 | Werge et al. |
| 5,484,421 | A | 1/1996 | Smocer |
| 5,496,274 | A | 3/1996 | Graves et al. |
| 5,509,911 | A | 4/1996 | Cottone, Sr. et al. |
| 5,520,665 | A | 5/1996 | Fleetwood |
| 5,535,785 | A | 7/1996 | Werge et al. |
| 5,573,516 | A | 11/1996 | Tyner |
| 5,584,314 | A | 12/1996 | Bron |
| 5,616,133 | A | 4/1997 | Cardenas |
| 5,616,136 | A | 4/1997 | Shillington et al. |
| 5,749,861 | A | 5/1998 | Guala et al. |
| 5,755,709 | A | 5/1998 | Cuppy |
| 5,775,671 | A | 7/1998 | Cote, Sr. |
| 5,817,063 | A | 10/1998 | Turnbull |
| 5,827,429 | A * | 10/1998 | Ruschke et al. ......... 210/321.75 |
| 5,968,020 | A | 10/1999 | Saito |
| 6,050,957 | A | 4/2000 | Desch |
| 6,050,978 | A | 4/2000 | Orr et al. |
| 6,096,024 | A | 8/2000 | Graves et al. |
| 6,261,266 | B1 | 7/2001 | Jepson et al. |
| 6,273,870 | B1 | 8/2001 | Garvin |
| 6,402,207 | B1 | 6/2002 | Segal et al. |
| 6,428,514 | B1 | 8/2002 | Goebel et al. |
| 6,500,153 | B1 | 12/2002 | Sheppard et al. |
| 6,544,235 | B2 | 4/2003 | Motisi et al. |
| 6,605,076 | B1 | 8/2003 | Jepson et al. |
| 6,612,624 | B1 | 9/2003 | Segal et al. |
| 6,743,214 | B2 | 6/2004 | Heil et al. |
| 6,988,510 | B2 | 1/2006 | Enerson |
| 7,040,598 | B2 | 5/2006 | Raybuck |
| 7,137,654 | B2 | 11/2006 | Segal et al. |
| 7,306,566 | B2 | 12/2007 | Raybuck |
| 7,651,481 | B2 | 1/2010 | Raybuck |
| 2003/0018301 | A1 | 1/2003 | Sheppard et al. |
| 2004/0158204 | A1 | 8/2004 | Reboul |
| 2004/0201216 | A1 | 10/2004 | Segal et al. |
| 2005/0087715 | A1 | 4/2005 | Doyle |
| 2006/0027270 | A1 | 2/2006 | Truitt et al. |
| 2006/0033331 | A1 | 2/2006 | Ziman |
| 2006/0237065 | A1 | 10/2006 | Enerson |
| 2007/0016161 | A1 | 1/2007 | Costa et al. |
| 2007/0179454 | A1 | 8/2007 | Ziman et al. |
| 2007/0260195 | A1 | 11/2007 | Bartholomew et al. |
| 2008/0045929 | A1 | 2/2008 | Birnbach |
| 2008/0058702 | A1 * | 3/2008 | Arndt et al. .............. 604/20 |
| 2008/0139950 | A1 | 6/2008 | Molnar et al. |
| 2008/0140020 | A1 | 6/2008 | Shirley |
| 2008/0140055 | A1 | 6/2008 | Shirley |
| 2008/0312640 | A1 | 12/2008 | Grant |
| 2008/0318456 | A1 | 12/2008 | Yow et al. |
| 2008/0319422 | A1 | 12/2008 | Cardenas |
| 2009/0099552 | A1 | 4/2009 | Levy et al. |
| 2009/0187166 | A1 | 7/2009 | Young |
| 2009/0318456 | A1 | 12/2009 | Herdewijn et al. |
| 2010/0286558 | A1 | 11/2010 | Schraga |

FOREIGN PATENT DOCUMENTS

| | | |
|---|---|---|
| EP | 1233809 B1 | 9/2004 |
| JP | 10-076005 | 3/1998 |
| JP | 2003-126269 | 5/2003 |
| JP | 2003-339876 | 12/2003 |
| WO | WO-2006/020635 | 2/2006 |
| WO | WO-2007/089531 | 8/2007 |

OTHER PUBLICATIONS

Non-Final Office Action in U.S. Appl. No. 12/711,641, mailed Jun. 23, 2011, 19 pgs.

Correspondence, *British Journal of Anaesthesia* 86(6) 2001, 896-904.

Anderson, MD, Ronald A. "Letter to the Editor: Infallible Measures Needed to Prevent Errors in the Administration of Chemotherapeutic Agents", *Medical and Pediatric Oncology 32* 1999, 401-402.

Katz, Leon "Inadvertent Misconnection of Medical Tubing: Protective Incompatibility", *Health and Welfare* Canada, Ottawa 1986, 2517-2518.

Lanigan, "Correspondence", *Anesthesia*, 56 2001, 585-610.

Sheppard, Ian "Medication Safety Alerts", *The Canadian Journal of Hospital Pharmacy*, vol. 57, No. 3 Jun. 2004, 4.

Toft, Prof., Brian "External Inquiry into the adverse incident that occurred at Queen's Medical Centre, Nottingham", *Department of Health* Jan. 4, 2001, 70 pgs.

Woods, Prof., Kent W. "The Prevention of Intrathecal Medication Errors—A report to the Chief Medical Officer", *Department of Healt* Apr. 2001, 20 pgs.

PCT International Search Report & Written Opinion in PCT/US2011/045281, mailed Apr. 19, 2012, 23 pgs.

Non-Final Office Action in U.S. Appl. No. 12/844,546, dated Jun. 25, 2012, 24 pgs.

Non-Final Office Action in U.S. Appl. No. 12/711,641, mailed Oct. 10, 2012, 15 pgs.

Non-Final Office Action in U.S. Appl. No. 12/711,641, dated Mar. 20, 2013, 10 pgs.

Final Office Action in U.S. Appl. No. 12/711,641, mailed Oct. 18, 2011, 10 pgs.

Non-Final Office Action in U.S. Appl. No. 12/711,641, dated Nov. 20, 2014, 10 pgs.

* cited by examiner

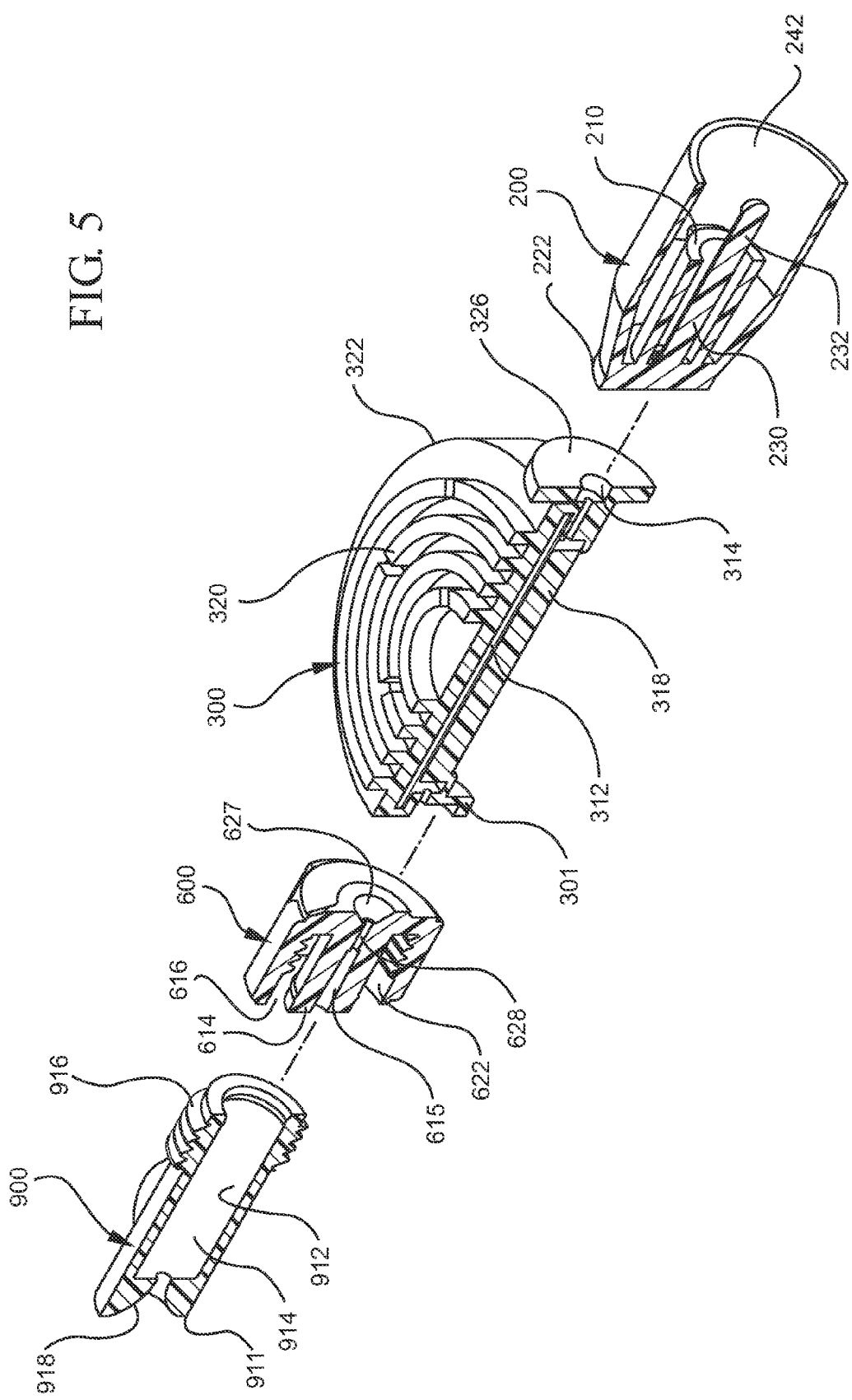

SAFETY DRUG DELIVERY SYSTEM

TECHNICAL FIELD

Aspects of the present invention relate to drug delivery systems for use with epidural anesthesia.

BACKGROUND

Administration of epidural anesthesia through a continuous procedure is widely used as a form of regional anesthesia for patient pain management. In such procedures, anesthesia drugs are injected into the epidural space through a catheter. During such continuous epidural anesthesia procedures, the patient may also have an intravenous line to receive other medications. Errors in delivering medication can occur when anesthesia drugs are introduced into an intravenous line or other types of medications are introduced to epidural space. Such errors may cause permanent damage to patients. Studies have shown that medication error rate for erroneously delivered anesthesia ranges from 0.1% to as high as 0.75% (see Stabile, M. et al., "Medical Administration in Anesthesia," *Anesthesia Patient Safety Foundation Newsletter*, Vol. 22, No. 3, (2007)).

Previous attempts at reducing errors in drug delivery include the use of labels or color coded devices to differentiate specific route-accessing devices (e.g., catheter connectors) and containers that contain medication (e.g., syringe and IV bags). Studies have shown that clinicians tend to ignore these labels and color codes. Other attempts to reduce error have required additional components that can be cumbersome for attachment. The use of additional components has also required the use of specialized syringe and/or catheter connections. Some configurations also preclude the use of filters and other safety components typically used during the administration of epidural anesthesia.

Accordingly, there is a need for a drug delivery system that can effectively (and physically) eliminate wrong-route medication error possibilities for use in all types of epidural anesthesia administration procedures that do not also require the use of additional and specialized components.

SUMMARY

In this disclosure, a convention is followed wherein the distal end of the device is the end closest to a patient and the proximal end of the device is the end away from the patient and closest to a practitioner.

A first aspect of the present application pertains to a drug delivery system including an actuator assembly attached to one end of a filter and a conduit attached to a second end of the filter. In accordance with one or more embodiments, the actuator assembly and the filter are integrally formed or permanently attached as a single unit.

In one or more embodiments, the actuator assembly has a distal end, a proximal end. The distal end of the actuator assembly includes a projection including an opening attached thereto. The projection extends in a proximal direction from the distal end of the actuator assembly. The projection may include two intersecting beams extending from the distal end of the actuator assembly to the proximal end of the actuator assembly. The actuator assembly according to one or more embodiments includes a hub attached to the distal end of the actuator assembly and disposed in a coaxial relationship with the projection. In one or more embodiments, the hub includes an open proximal end for receiving an open end of a container, for example, a tip of a syringe barrel. The hub may include a luer lock structure for engaging a container comprising a luer lock fitting or a luer slip structure for engaging a container including a luer slip fitting. The actuator assembly may optionally include a shield attached to the distal end of the actuator assembly that surrounds the hub in a coaxial relationship.

The filter that is attached to the distal end of actuator assembly may include an inlet that is permanently attached to the actuator assembly and an outlet in fluid communication with the inlet and the opening of the projection. In one or more embodiments, the filter is disposed along a first axis. The filter includes a housing including a cavity that holds or contains filter material. In one or more embodiments, the housing is formed from a top plate and a bottom plate that are welded together or otherwise joined together. In accordance with one or more embodiments, the top plate and bottom plate of the housing may be arranged parallel to the first axis. In a more specific embodiment, the top plate and bottom plate are arranged perpendicularly to the first axis. The filter may also utilize a housing that includes a cylindrical body.

According to one or more embodiments, the conduit is attached to the outlet of the filter and may be used to attach the drug delivery system a delivery site. In one or more embodiments, the conduit comprises a luer fitting. The conduit may also include an adaptor for securing a non-luer fitting to the outlet of the filter. In one or more embodiments, the non-luer fitting includes a Tuohy-Borst adapter.

A second aspect of the present invention pertains to a method of administering medication to a delivery site. In one or more embodiments, the method includes providing a drug delivery system comprising an actuator assembly having a proximal end and a distal end that is permanently attached to an inlet of a filter, attaching the outlet of the filter to a delivery site and attaching an open end of a container including a medication to the actuator assembly. In one or more embodiments, the delivery site may include an epidural catheter. In one or more embodiments, the container includes a syringe barrel and/or a drug delivery container and the medication may include epidural anesthesia. Suitable containers may include a one-way valve that prevents fluid communication between the container and the opening of the projection.

In a specific embodiment, the filter of the actuator assembly includes an outlet in fluid communication with the inlet. The actuator assembly may include a projection with an opening in fluid communication with the outlet of the filter. The projection may extend in a proximal direction from the distal end of the actuator assembly. The actuator assembly may also include a hub attached to the distal end of the actuator assembly and extending in the proximal direction in a coaxial relationship with the projection. In one or more embodiments, the step of attaching an open end of a container to the actuator assembly includes inserting the projection into the open end of the container and securing the hub to the open end of the container.

BRIEF DESCRIPTION OF THE DRAWINGS

FIG. 5 illustrates a cross-sectional view of the drug delivery system and conduit shown in FIG. 4 taken along line 5-5;

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Aspects of embodiments of the present invention pertain to a drug delivery system including a conduit for attachment of the drug delivery system to a catheter or other delivery site, a filter and an actuator assembly.

In accordance with one aspect of the present invention, the filter and actuator assembly are integrally formed or permanently attached. In one or more embodiments, the conduit may be integrally formed or permanently attached to the filter and actuator assembly. In one or more embodiments, the drug delivery system permits attachment to catheters using a Tuohy-Borst adapter or other attachment adapter known in the art. A second aspect of the present invention pertains to a method of using the drug delivery systems described herein. Embodiments of each aspect will be described in further detail below.

Figure 17:
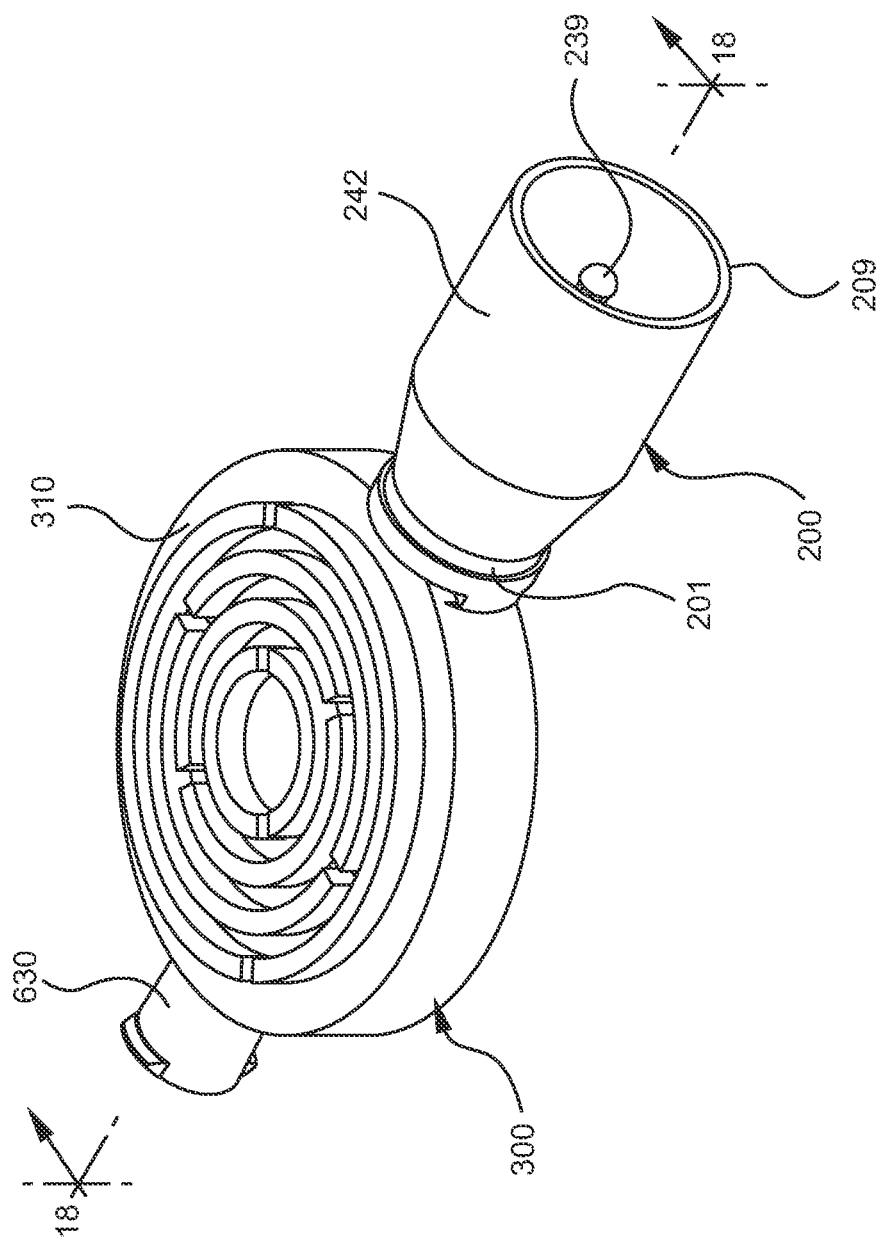
FIG. 17 illustrates a drug delivery system and standard luer fitting according to one or more embodiments.
Figure 18:
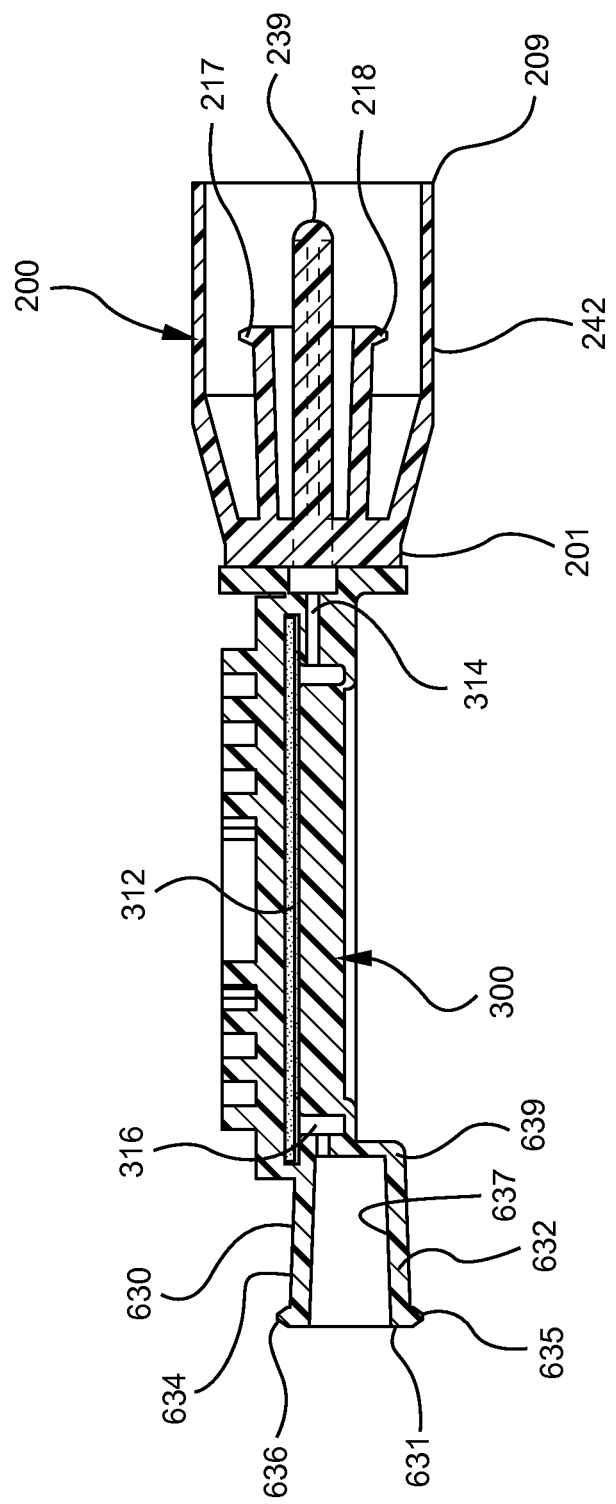
FIG. 18 illustrates a side cross-sectional view of the drug delivery system and conduit shown in FIG. 17 taken along line 18-18.

In one or more embodiments, the filter is disposed between the conduit and the actuator assembly, as shown in FIG. 1-20. Specifically, FIGS. 1-5 illustrate a configuration of a drug delivery system 100 according to one or more embodiments in which an actuator assembly 200 and a filter 300 are integrally formed and/or permanently attached along a first axis. FIGS. 8-12 illustrate a configuration of a drug delivery system 110 according to one or more embodiments in which the actuator assembly 200 and a filter 400 are integrally formed and/or permanently attached along a second axis. FIGS. 13-16 illustrate a configuration of a drug delivery system 120 according to one or more embodiments in which the actuator assembly 200 and a filter 500, including a housing with a cylindrical body, are integrally formed and/or permanently attached along a first axis. FIGS. 1-16 also illustrate a conduit 600 including an adaptor 610 that may be provided as a separate component or integrally and/or permanently attached to the filter 300. FIGS. 17-18 illustrate a conduit 600 including a standard luer fitting 630.

A first aspect of the present invention pertains to a drug delivery system comprising an actuator assembly 200 that is integrated with a filter. FIGS. 1-20 illustrate the actuator assembly 200 according to one or more embodiments. The actuator assembly 200 of one or more embodiments comprises a hub 210 for connecting an actuator 230 to a drug delivery connector or container containing epidural anesthesia or other medication. In embodiments where the actuator assembly 200 is connected to a drug delivery connector that is attached to a container, the actuator 230 permits fluid communication between the container and the filter. In one or more embodiments, the actuator assembly 200 may be utilized to open any one-way or check valves disposed within some drug delivery connectors and/or containers. As used herein, the term "one-way valve" includes any valves which permit fluid flow in one direction. As used herein, the terms "check valve" may be used interchangeably with the term "one-way valve." The actuator assembly may also be used with drug delivery connectors, containers and/or other devices that are free of valves or closures.

Figure 1:
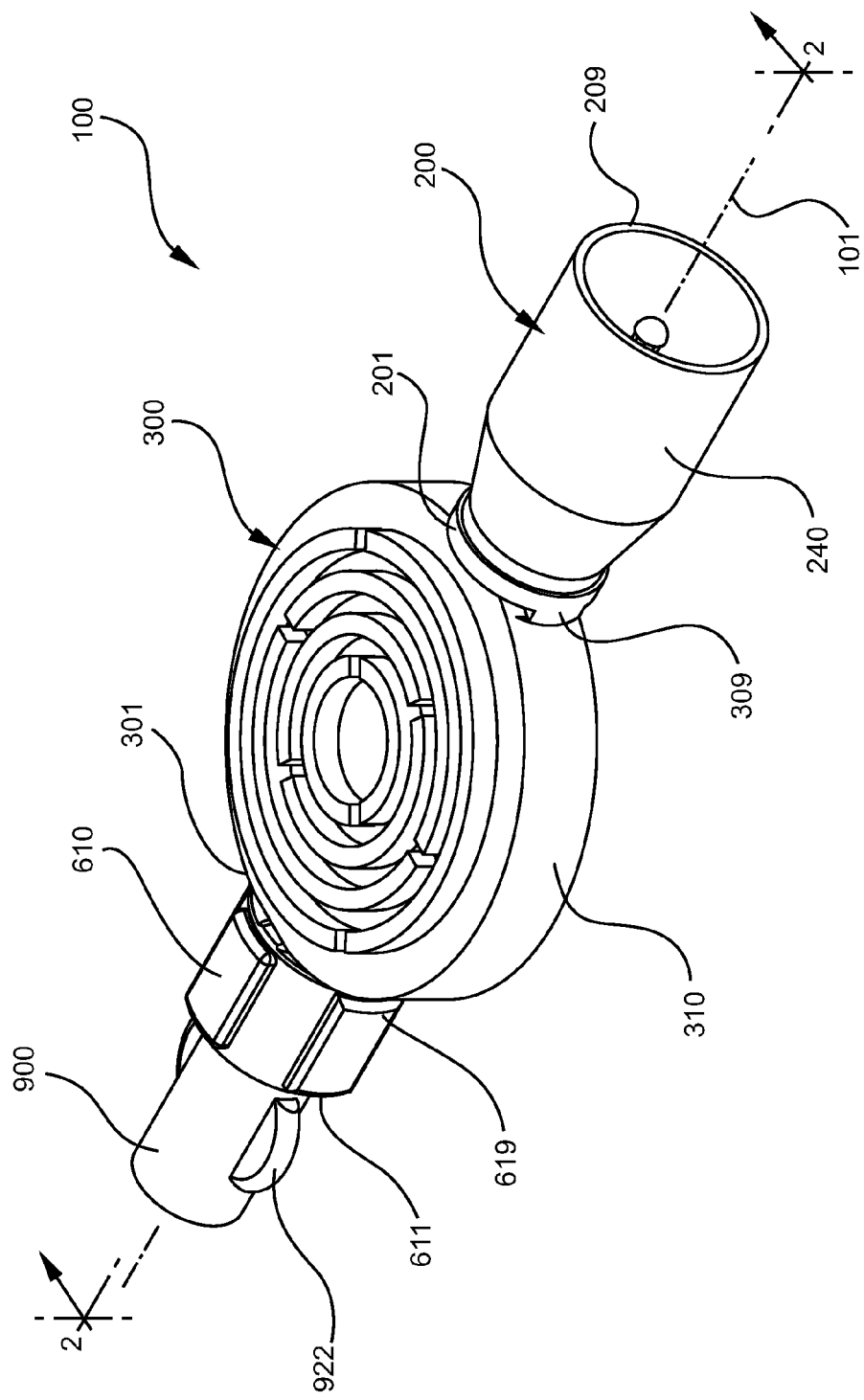
FIG. 1 illustrates a perspective view of a drug delivery system including a conduit according to one or more embodiments of the present invention.
Figure 2:
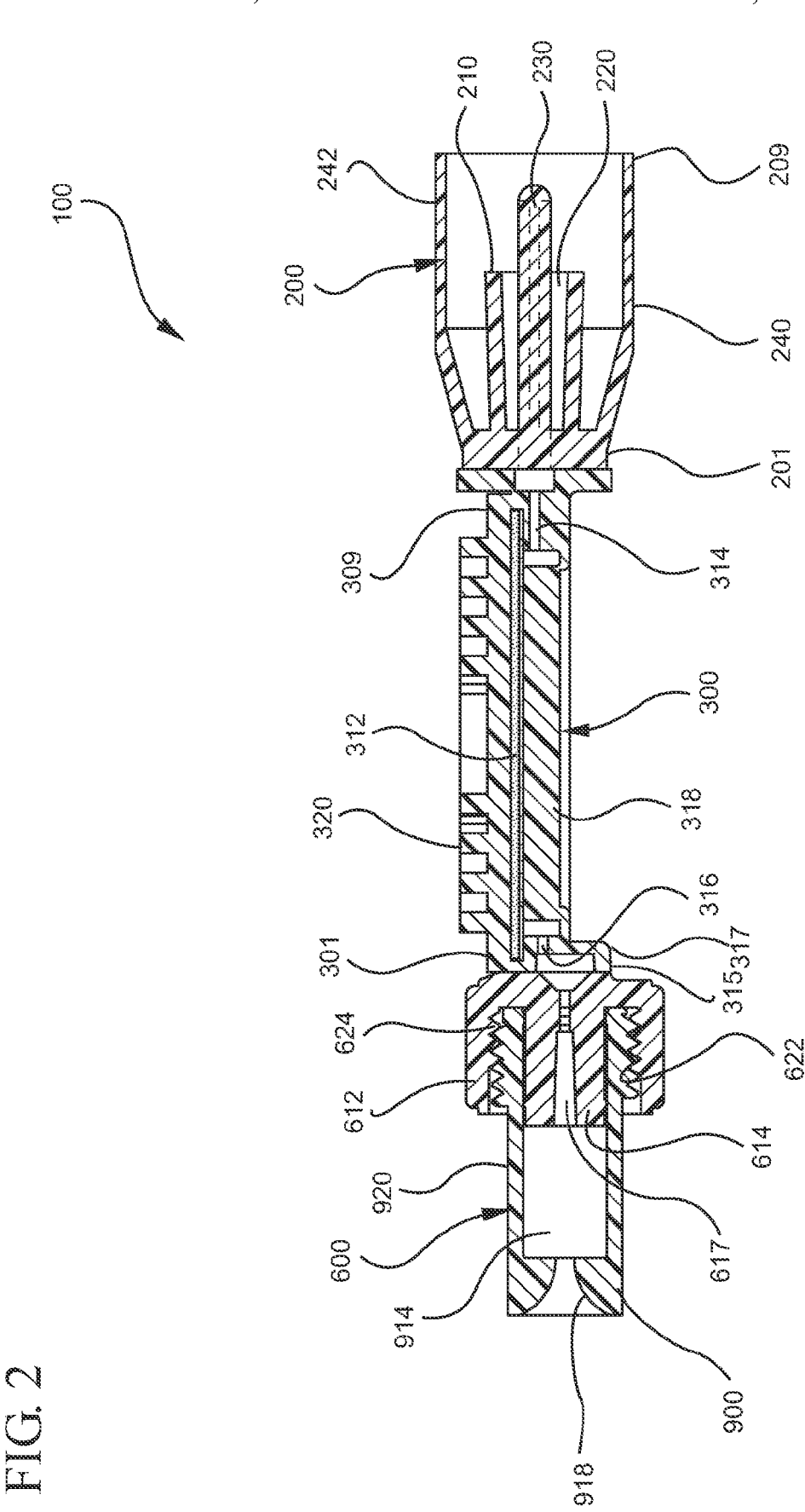
FIG. 2 shows a side cross-sectional view of the drug delivery system and conduit of FIG. 1 taken along line 2-2.
Figure 3:
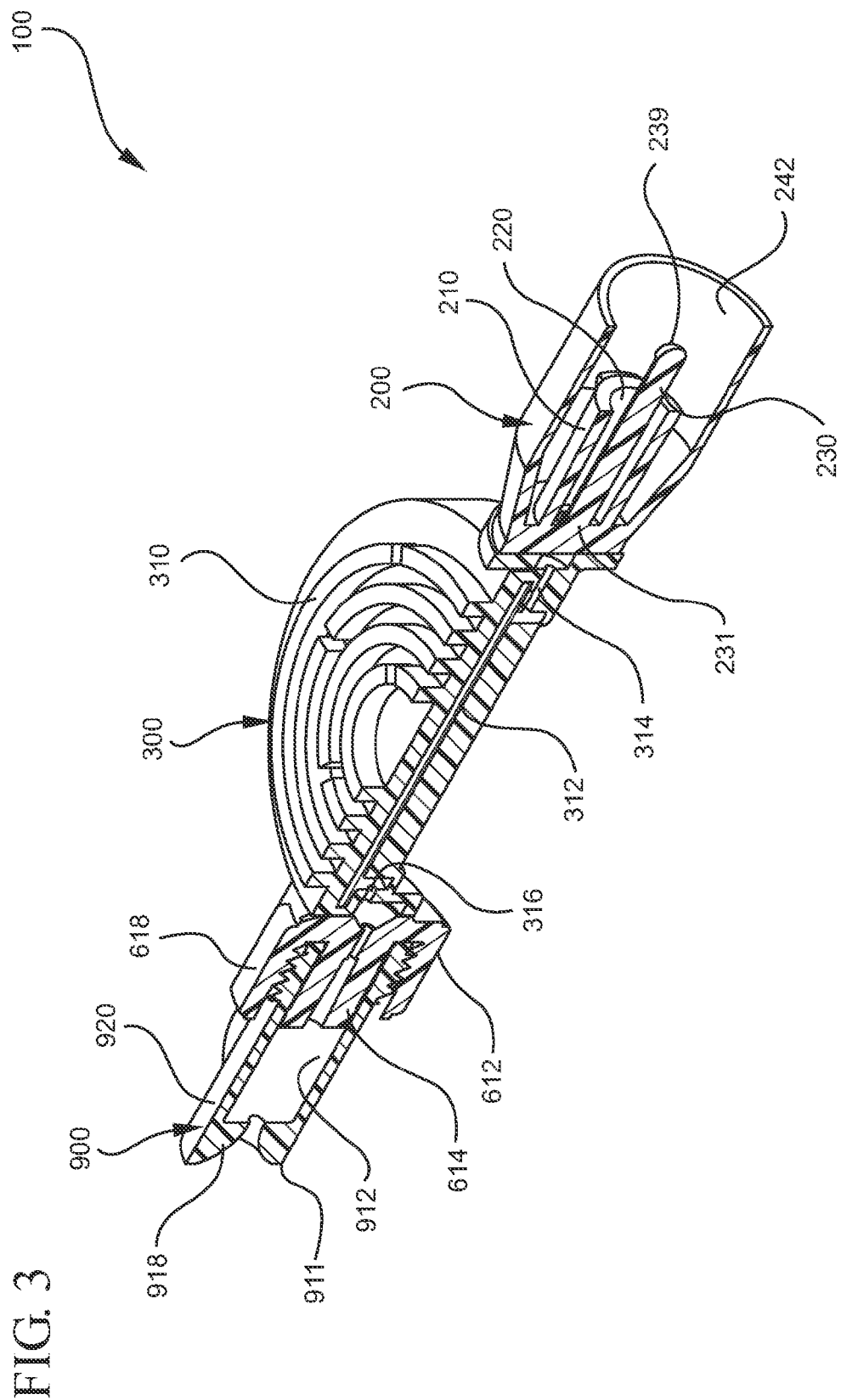
FIG. 3 shows a perspective view of the drug delivery system and conduit of FIG. 2.
Figure 4:
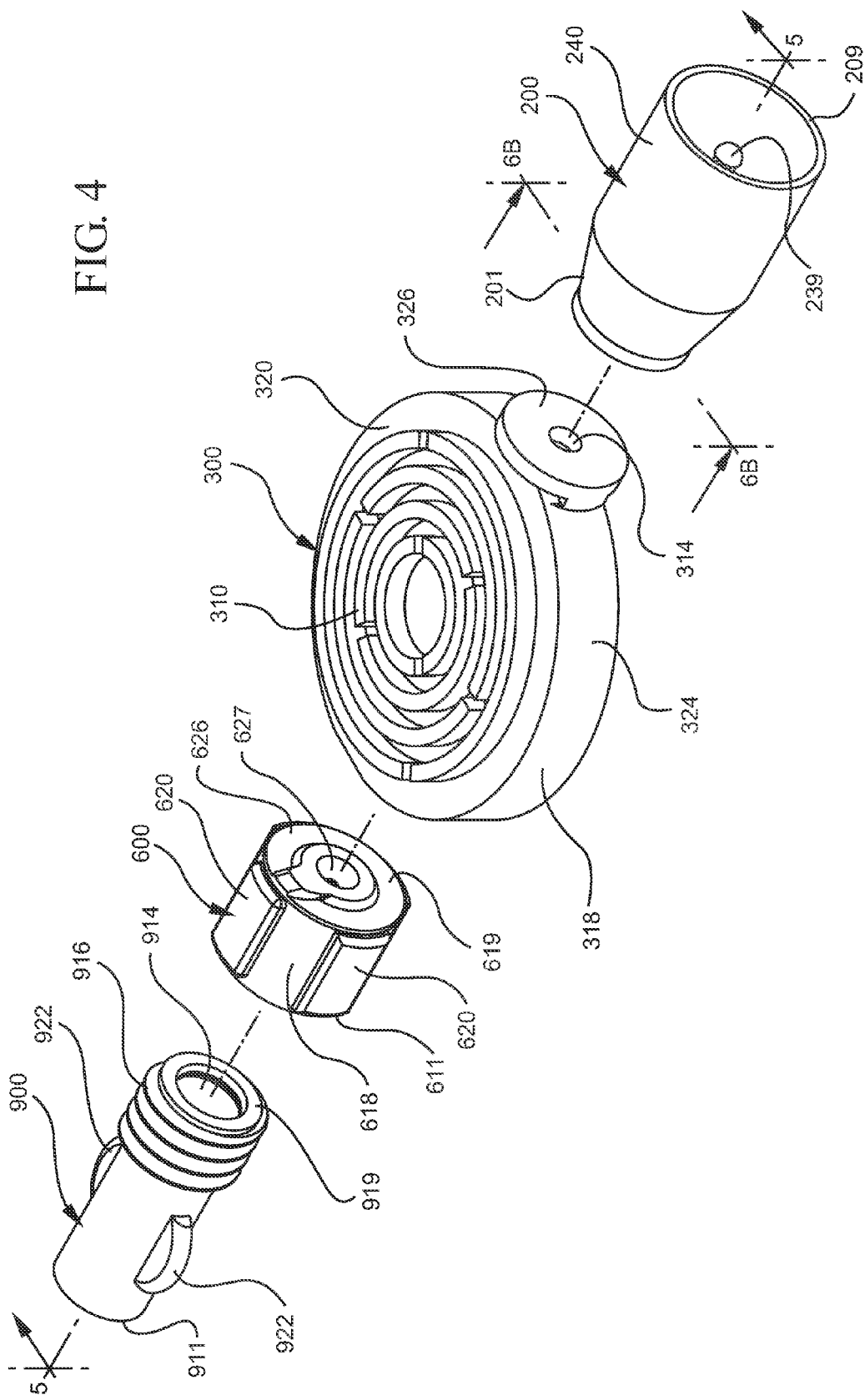
FIG. 4 illustrates a disassembled view of the drug delivery system and conduit shown in FIG. 1.
Figure 6B:
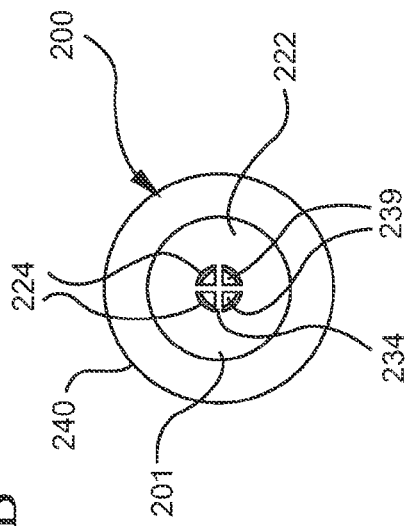
FIG. 6B illustrates a cross-sectional view of the drug delivery system taken along lines 6B-6B.
Figure 7B:
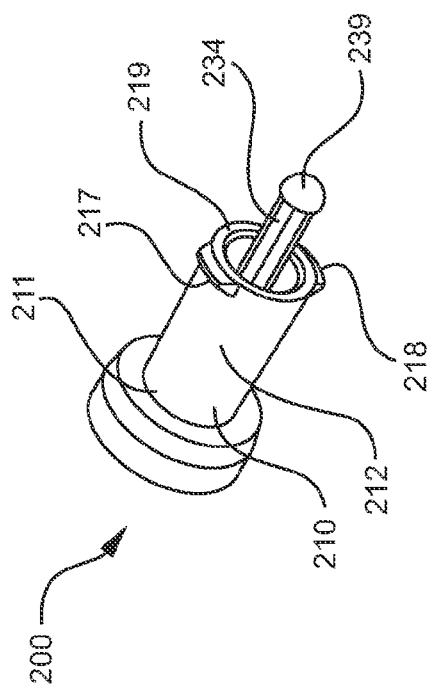
FIG. 7B shows a perspective view of the actuator assembly illustrated in FIG. 7A.
Figure 6A:
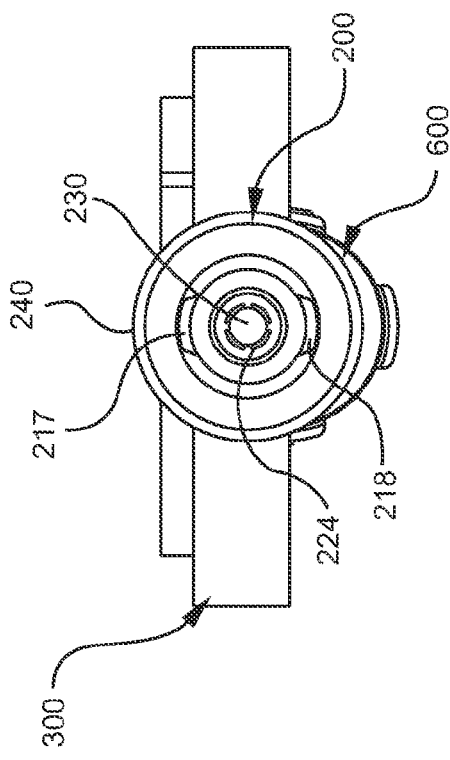
FIG. 6A illustrates the proximal end of the drug delivery system shown in FIG. 1.
Figure 7A:
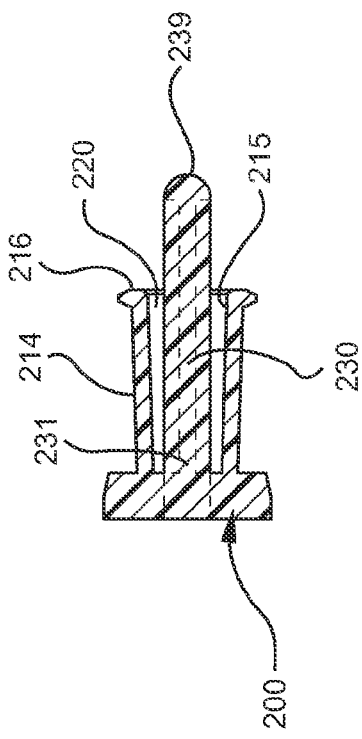
FIG. 7A illustrates a cross-sectional view of an actuator assembly according to one or more embodiments.

As shown in more detail in FIGS. 2, 7A and 7B, the actuator assembly 200 includes a distal end 201, a proximal end 209. The hub 210 includes a distal end 211, including a base 222, and a proximal end 219. The base 222 of the hub 210 is attached to the distal end 201 of the actuator assembly 200. The actuator 230 is shown in FIGS. 1-20 and includes a distal end 231, which is attached to the base 222 at the distal end 211 of the hub 210 and in fluid communication with the distal end 211 of the hub and a proximal end 239. The base 222 includes plurality of inlets 224 permitting fluid communication between the hub 210 and the actuator 230. In one or more embodiments, the plurality of inlets 224 are formed from an opening in the base 222 and the actuator 230, as will be more fully described below. The actuator 230 also includes a projection 232 extending from the distal end 231 to the proximal end 239 of the actuator 230. The proximal end 239 actuator 230 is unattached to any structure and may be described as "cantilevered" or supported on only one end. The proximal end 239 of the actuator 230 may include a blunt tip or rounded tip, as shown in FIG. 6A. In one or more embodiments in which the actuator assembly 200 is utilized to open a one-way valve within a container or drug delivery connector, the proximal end 239 of the projection 232 may be shaped to cooperate with a one-way valve to facilitate opening of the one-way valve or to control the rate at which the one-way valve is opened to control flow rate.

In one or more embodiments, the proximal end 239 of the actuator 230 has an outer diameter that is larger than the inner diameter of standard luer slip connections utilized in most IV medication delivery syringes to prevent accidental connection of IV medication-containing syringes or container with the actuator assembly 200 and to prevent access to the anesthesia catheter or other inappropriate delivery sites for IV medication-containing syringes or containers.

In one or more embodiments, the projection 232 of the actuator assembly has a length which, upon attachment of the actuator assembly 200 to a drug delivery connector and/or container, permits the proximal end 239 of the actuator 230 to extend into a drug delivery connector and/or container and facilitate the flow of medication contained therein to the filter, as will be more fully described herein. In a specific embodiment, the projection 232 facilitates the flow of medication by opening any one-way valves in the drug delivery connector and/or container. For example, when the projection 232 is inserted into an opening or open end of a drug delivery connector and/or container and the actuator 230 is attached to the drug delivery connector and/or container, the proximal end 239 of the actuator extends into the drug delivery connector and/or container and exerts a force on a valve present within the drug delivery connector and/or container to open the valve and allow fluid communication between the drug delivery connector and/or container and the filter.

The projection 232 includes one or more openings 234, as shown in FIG. 6B extending the length of the projection 232 from the proximal end 239 to the distal end 231 of the actuator 230 to permit fluid communication between a drug delivery connector and/or container and the filter. Specifically, the one or more openings 234 permit the medication to flow from the drug delivery connector and/or container to the plurality of inlets 224 on the base 222 of the hub 210 and a filter, to a delivery site attached to the drug delivery system 100. In one or more embodiments, the projection 232 is in the form of two perpendicularly intersecting beams that extend in the proximal direction and define four openings 234 at the distal end and at free proximal end 239 of the actuator 230. As shown in FIG. 6B, the distal end 231 of the actuator 230 is attached to the base 222 such that the projection 232 covers the opening of the base 222 dividing the opening into a plurality of inlets 224. The plurality of inlets 224 are in fluid communication with the openings 234 of the projection 232. In one or more embodiments, the intersecting beams may include a solid end at the proximal end 239 of the actuator 230. In one or more embodiments, the solid end is in the form of a hemi-sphere. In a specific embodiment, the projection 232 is in the form of a single, proximally extending beam (not shown) that defines two openings 234. In a more specific embodiment, the projection 232 includes a hollow member (not shown) with opposing open ends that extends proximally and includes an open path (not shown) extending from the distal end 231 to the proximal end 239 of the actuator.

In the embodiment shown in FIG. 1-20, the hub 210 is attached to the distal end 231 of the actuator 230 and includes a wall 212 extending from the proximal end 219 to the distal end 211. The distal end 231 of the actuator 230 is attached to the base 222 at the distal end 211 of the hub 210 and extends along the length of the hub 210 and beyond the proximal end 219. In one or more embodiments, the wall 212 includes having an outside surface 214 that includes a luer lock structure 216. In a specific embodiment, the luer lock structure 216 includes at least one radially outwardly extending portion that engages a threaded portion disposed on an inside surface of a corresponding luer lock fitting on the drug delivery connector or container. In the embodiments shown in FIGS. 7A and 7B, the radially outwardly extending portion includes two radially outwardly extending tabs 217, 218. In an even more specific embodiment, the radially outwardly extending portion includes a peripheral lip (not shown). In one or more embodiments, the wall includes an inside surface 215 that includes a luer slip structure (not shown). In a specific embodiment utilizing a luer slip structure (not shown), the inside surface 215 of the wall 212 may define a tapered cross-sectional width that increases from the distal end 211 to the proximal end 219 and is shaped and/or contoured to frictionally engage a standard luer slip male fitting (not shown) that may be incorporated or used with one or more embodiments of a drug delivery connector and/or container.

In one or more embodiments, the wall 212 of the hub 210 is formed in a coaxial relationship to the projection 232 of the actuator 230 and defines a channel 220 between the hub 210 and the projection 232. The hub 210 may be securely engaged to an opening of a drug delivery connector and/or container by inserting the projection 232 into an opening of the drug delivery connector and/or container by inserting the proximal end 239 of the actuator 230 into the opening. Where the hub 210 utilizes a luer lock structure 216, the drug delivery connector and/or container may be rotated with respect to the hub and vice versa so the tabs 217, 218 engage the a corresponding threaded portion at the opening of the drug delivery connector and/or container. In embodiments of the hub 210 utilizing a luer slip structure (not shown), the opening of the drug delivery connector and/or container is inserted into the channel 220 of the hub 210 until sufficient frictional interference is formed between the drug delivery connector and the inside surface 215 of the hub 210.

In the embodiment shown in FIGS. 1-20, the projection 232 has an axial length that allows the proximal end 239 of the actuator 230 to enter a drug delivery connector and/or container and exert a proximally directed force on any one-way valves present within the drug delivery connector and/or container. The one-way valve is positioned in a closed position due to the force exerted by the medication within the drug delivery connector and/or container in the distal direction. In one or more embodiments, the projection 232 is may be utilized to apply a force on the one-way valve in a direction opposite the direction of fluid flow from the drug delivery connector and/or container. Specifically, when the actuator assembly 200 is attached to the opening of the drug delivery connector and/or container, the hub 210 is engaged with the drug delivery connector and/or container by utilizing the luer lock structure 216 or the luer lock structure (not shown). During engagement of the hub 210 and the drug delivery connector and/or container, the projection 232 extends into the opening of the drug delivery connector and/or container and exerts a force on the one-way valve in the proximal direction, thus opening the one-way valve to permit fluid flow from the drug delivery connector and/or container through the openings 234 in the projection 232 and to the actuator assembly 200. In one or more embodiments, the force exerted on the one-way valve in the proximal direction by projection 232 is greater than the force exerted on the one-way valve in the distal direction by the medication within the drug delivery connector and/or container.

The amount of force exerted on the one-way valve may be adjusted to control or meter the flow rate of the medication through the projection 232. In accordance with one or more embodiments, the length of the projection 232 may be adjusted to control or meter the amount of force exerted on the one-way valve to control or meter the flow rate of the medication contained within the container and/or the drug delivery connector. In one or more embodiments, the projection 232 may be modified to have a length that causes proximal movement of the one-way valve prior to full attachment of the hub 210 and the drug delivery connector and/or container. In a specific embodiment, the projection 232 may be modified to have a length that causes proximal movement of the one-way valve when the hub 210 is fully attached to the drug delivery connector and/or container.

In one or more embodiments, the length of the hub 210 may be adjusted to control or meter the amount of force exerted on the one-way valve to control or meter the flow rate of the medication contained within the container and/or of the drug delivery connector. In such embodiments, the user may control the flow rate by the amount and direction of rotational force used to engage the hub 210 and container and/or drug delivery connector. The shape and dimensions of the projection 232 may also be modified to permit connection to specific containers or drug delivery connectors to avoid accidental connections and medication errors. In one or more embodiments, the outer diameter of the projection 232 at the proximal end 239 of the actuator may be shaped or sized to prevent accidental connection with other types of containers, for example, syringes containing IV medication.

In one or more embodiments, the actuator assembly 200 may include a shield 240, as shown in FIGS. 1-6. The shield 240 may be used to guide the connection between the actuator assembly 200 and a drug delivery connector and/or container. In one or more embodiments, the shield 240 may protect the projection from lateral pressure, which may cause the projection 232 to be bent or broken during handling/shipping. The shield 240 may also prevent contamination of the projection 232.

In one or more embodiments, the shield 240 may be provided in the form of a peripheral wall 242 surrounding the hub 210. The peripheral wall 242 may be formed to permit space between the hub 210 and peripheral wall 242 to accommodate any external structures of the drug delivery connector and/or container. In one or more embodiments, the peripheral wall 242 may have a constant cross-sectional width. In a specific embodiment, the peripheral wall 242 may have a tapered cross-sectional width increasing from the distal end 201 of the actuator assembly 200 to the proximal end of the actuator assembly 200. The peripheral wall 242 may have an expanded cross-sectional width proximally adjacent to the tapered cross-sectional width. The length of the peripheral wall 242 may extend from the distal end 201 of the actuator assembly beyond the proximal end 219 of the hub. In a more specific embodiment, the peripheral wall 242 may have a length that terminates between the proximal end 219 of the hub 210 and the proximal end 239 of the actuator 230. In a specific embodiment, the length of the peripheral wall 242 terminates at the proximal end 239 of the actuator. In an even more specific embodiment, the length of the peripheral wall terminates beyond the proximal end 239 of the actuator.

In one or more embodiments, the peripheral wall 242 may be composed of a clear material providing visual indication of complete connection between the hub 210 and a drug delivery connector and/or container. The peripheral wall 242 may be composed of an extruded or molded plastic material. In another alternative embodiment, the peripheral wall 242 may be removable from the actuator assembly 200.

Figure 19:
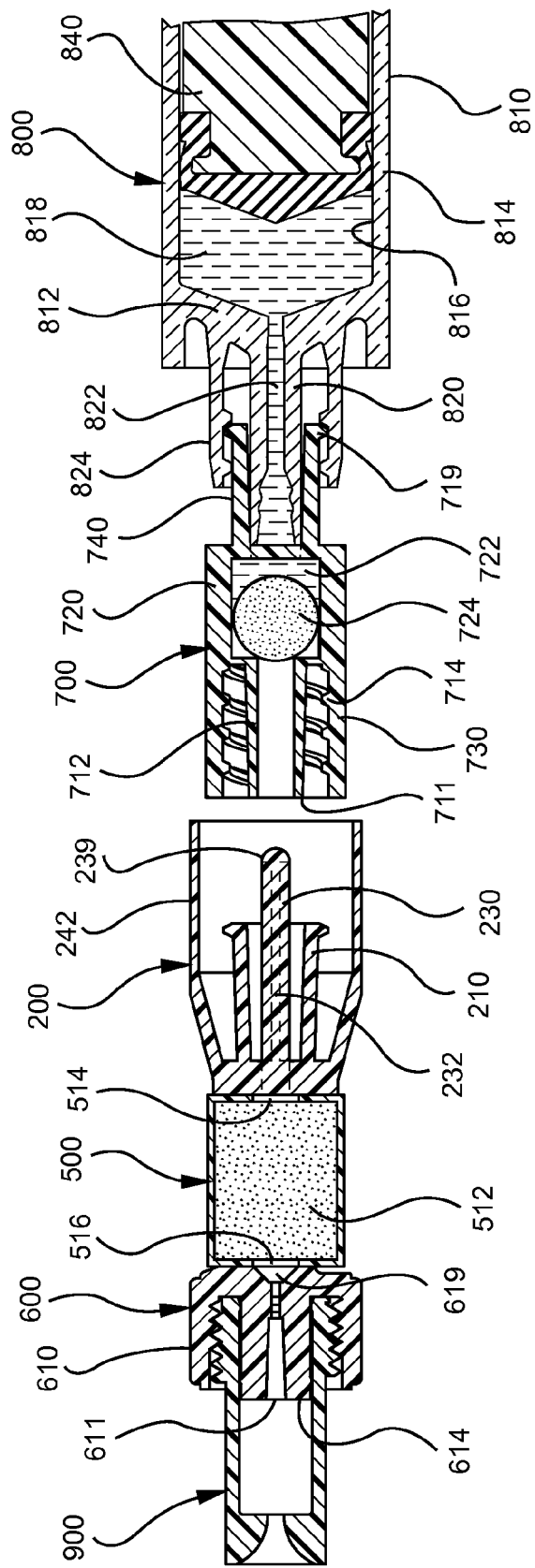
FIG. 19 illustrates the drug delivery system shown in FIG. 14 and a cross-sectional view of a drug delivery connector and syringe according to one or more embodiments.
Figure 20:
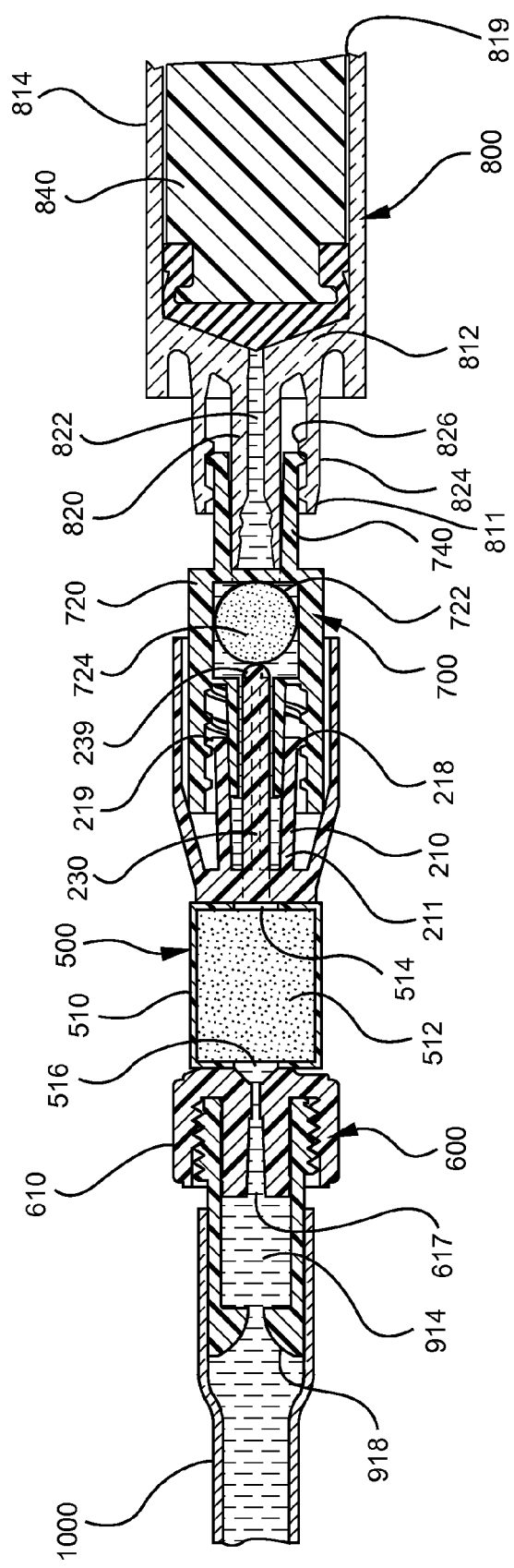
FIG. 20 illustrates the drug delivery system, drug delivery connector and syringe shown in FIG. 19 assembled to a catheter.

Compatible drug delivery connectors that may be used with the drug delivery connectors described herein include any adapters used to engage a filter to a fluid source or container, for example, syringes, epidural drug bag, or extension tubing connector from the epidural infusion pump. An example of a drug delivery connector 700 is shown in FIGS. 19-20 and includes an open distal end 711, an open proximal end 719 and a housing 720 defining a cavity 722 in fluid communication with the open distal end 711 and the open proximal end 719. In the embodiment shown in FIGS. 19-20, the cavity 722 includes a valve 724 that seals access to the cavity 722 from the open distal end 711. The valve 724 also prevents fluid communication between the open proximal end 719 and the open distal end 711. The open distal end 711 includes a distal connection portion 730 for attaching the drug delivery connector 700 to the actuator assembly 200 and the open proximal end 719 includes a proximal connection portion 740 for attachment of a container to the drug delivery connector 700. In the embodiment shown, the open distal end 711 of the drug delivery connector 700 includes a luer lock fitting including a tip 712 and a threaded collar 714 surrounding the tip 712. In an alternative embodiment, the open distal end 711 may include a luer slip fitting (not shown).

For illustration, a syringe 800 is shown in FIG. 19-20 as an example of a container suitable for use with the drug delivery systems and/or drug delivery connectors described herein. In one or more embodiments, a compatible syringe 800 includes a syringe barrel 810 including an open proximal end 819 and a distal end 811 and an end wall 812. A sidewall 814 extends from the distal end 811 to the open proximal end 819 and includes an interior surface 816 that defines a chamber 818 for holding fluids, which may include liquid medication. The distal end 811 may also include a tip 820 having an open passageway 822 therethrough in fluid communication with the chamber 818. The tip may include a luer slip fitting (not shown) or, as illustrated in FIGS. 19-20, may include a luer lock fitting including a coaxial collar 824 including a threaded section 826. The syringe 800 may also include a plunger rod 840 inserted into the open proximal end 819 of the syringe barrel 810 to aspirate epidural anesthesia into the chamber 818 of the syringe barrel 810 and to expel the epidural anesthesia from the chamber 818 of the syringe barrel 810. In one or more embodiments, the syringe may incorporate a valve (not shown) in the chamber 818. It is to be understood that the configuration shown is merely exemplary, and the components can be different in shape and size than shown.

The syringe 800 may be prefilled or empty and require filling prior to use with the drug delivery systems described herein. A hypodermic needle including a needle cannula with a lumen or opening therethrough may be attached to the tip 820 of the syringe barrel 810 to aspirate epidural anesthesia into the syringe barrel 810. In embodiments where the syringe 800 includes a drug delivery connector, the hypodermic needle may be attached to the open distal end of the drug delivery connector, as described above. The hypodermic needle may also be attached to the syringe 800 or drug delivery connector 700 using a luer fitting.

In embodiments of the drug delivery connector 700 and/or syringe 800 which may incorporate a valve, the flow of medication during aspiration exerts a force on the one-way valve in a proximal direction and opens the one-way valve to permit medication to enter the drug delivery connector and/or the syringe. To attach the filled syringe to the actuator assembly 200, the needle hub is removed. After removal of the needle hub, the force of the medication filled in the syringe exerts a force on the one-way valve present in either the drug delivery connector 700 or the syringe 800 (not shown) in the distal direction and closes fluid communication between the drug delivery connector 700 and/or syringe 800. When the one-way valve is closed, the liquid is prevented from leaking out.

When the medication within the syringe barrel 810 and/or drug delivery connector 700 is to be delivered to a delivery site, such as a catheter 1000, as shown in FIGS. 19-20, the actuator assembly 200 is assembled to the tip 820 of the syringe or the open distal end 711 of the drug delivery connector. During assembly, the projection 232 is inserted into the 820 tip and/or open distal end 711 until it extends into the chamber 818 of the syringe 800 or cavity 722 of the drug delivery connector 700. In embodiments which utilize a syringe 800 and/or a drug delivery connector 700 with a luer slip tip (not shown), the inside surface 215 of the hub 210 frictionally engages the luer slip tip. In embodiments, which utilize a syringe with a luer lock tip, the luer lock structure 216 of the hub 210 engages with the threaded section 826 of the coaxial collar 824 of the syringe 800 or the threaded collar 714 of the drug delivery connector 700. The first aspect of the drug delivery system also includes a filter integrally formed or permanently attached to the distal end 201 of the actuator assembly 200. The presence of the actuator assembly permits connection between the filter and only specific drug delivery connectors and/or containers. Integration of the filter and actuator assembly reduces the risk of misconnection between the filter and a standard luer syringe. The integration of the filter and actuator assembly in a drug delivery system forces the use of a filter when administering epidural anesthesia, which reduces infection risk. Further, the integration of the filter and actuator system provides ease of use because it eliminates the need for a practitioner and/or user to assemble these parts for use. The integrally formed or permanently attached filters and actuator assemblies described herein eliminate the need for additional clamping components or attachment components to ensure a fluid-tight connection between the filter and actuator assembly and avoid leakage issues.

FIGS. 1-5 illustrate a filter 300 according to one or more embodiments of the present invention. The filter 300 includes a distal end 301 and a proximal end 309. The filter 300 also includes a housing 310 that defines a cavity 312 and is integrally molded to the distal end 201 of the actuator assembly 200. The inlet 314 may be integrally permanently glued or welded to the base 222 at the distal end 211 of the hub 210. The filter 300 includes an inlet 314 and an outlet 316 through which the medication entering the openings 234 on the projection 232 and the plurality of inlets 224 of the hub 210 may enter the housing 310 and exit the housing 310.

In the embodiments illustrated in FIG. 1-5, the housing 310 includes two plates 318, 320 that are joined together. The plates may be formed from a polymer materials such as polycarbonate to form a cavity 312. In a specific embodiment, the plates 318, 320 are welded together, for example, using ultrasonic welding techniques known in the art, and/or glued together, using methods known in the art. In the embodiment shown in FIGS. 1-5, the plates 318, 320 are identical and include a peripheral edge 322 and are concavely shaped. In one or more embodiments, one or both of the plates 318, 320 may have different shapes and/or sizes. In the embodiment shown in FIG. 1, each plate 318, 320 may also include an edge wall 324 extending from the peripheral edge 322 at an angle of about 90 degrees with respect to the plate 318, 320. In one or more embodiments, the edge wall 324 extends perpendicularly and outwardly from the peripheral edge 322 of the plates 318, 320. In a specific embodiment, the angle of the edge wall 324 with respect to each plate is in the range from about 45 degrees to 180 degrees. In a more specific embodiment, the angle of the edge wall 324 with respect to the plate is in the range from about 45 degrees to about 135 degrees. To form the housing, the edge walls 324 of the plates 318, 320 are joined to form a cavity 312 having a disc shape.

In a specific embodiment, one of the plates 318, 320 may include an edge wall 324 while the second of the plates 318, 320 is free of an edge wall 324. In such embodiments, to form the housing 310, the edge wall 324 of one of the plates 318, 320 is joined to the peripheral edge 322 of the other plate 318, 320. In a more specific embodiment, both plates 318, 320 are free of an edge wall 324 and a separate edge wall 324 component having a first rim (not shown) and second rim (not shown) is used to join the plates 318, 320. In such embodiments, the first rim (not shown) is welded to the peripheral edge 322 of one of the plates 318, 320 and the second rim (not shown) of the edge wall 324 is welded to the peripheral edge 322 of the other plate 318, 320.

In one or more embodiments, the inlet 314 and/or the outlet 316 may be formed on the edge wall 324. In such embodiments, the housing 310 may be attached to the actuator assembly 200 with the plates 318, 320 in a horizontal alignment or in parallel arrangement with respect to the actuator assembly and the first axis 101, as shown in FIGS. 1-5. In an alternative embodiment, the plates 318, 320 may be disposed in a horizontal alignment or in parallel arrangement with respect to the actuator assembly and the first axis 101 where the inlet 314 and outlet 316 are formed on the plates 218, 320.

The inlet 314 may be disposed at an opposite end of the edge wall 324 from the outlet 316 or may be disposed at other locations along the edge wall 324. In a specific embodiment, the inlet 314 formed from a partial cut out of the edge wall 324 on the opposite end of the edge wall 324 from the peripheral edge 322 of one or both plates 318, 320. Similarly, the outlet 316 may also be formed from a partial cut out of the edge wall 324 on the opposite end of the edge wall 324 from the peripheral edge 322 of one or both plates 318, 320. When the plates 318, 320 are joined, the partial cut outs of the inlet 314 and outlet 316 would be aligned to form a single inlet 314 and single outlet 316. In a more specific embodiment the inlet 314 and/or outlet 316 include apertures (not shown) formed on the edge wall 324 that are completely surrounded by the edge wall 324. In such embodiments, the inlet 314 and/or outlet 316 are intact despite the alignment of the plates 318, 320, with respect to each other. In an alternative embodiment, the housing 310 may be integrally molded to form a cavity 312 having a disc shape.

In the embodiments shown in FIGS. 1-5, the inlet 314 may include a neck 326 surrounding the inlet 314. In one or more embodiments, the neck 326 provides support for attachment of the filter 300 and, specifically, the inlet 314, to the base 222 at the distal end 211 of the hub and/or open distal end 201 of the actuator assembly.

FIGS. 8-12 illustrate a filter 400 according to one or more embodiments of the present invention which is positioned along a second axis 102. The filter 400 includes an inlet 414 and an outlet 416 through which the medication entering the openings 234 on the projection 232 may enter a housing 410 and exit the housing 410. The housing 410 includes two plates 418, 420 that are joined together forming a cavity 412. As with filter 300 above, the housing 410 may be integrally molded. As also described above with reference to the filter 300, an edge wall 424 may be utilized to join the plates 418, 420. The edge wall 424 may extend from a peripheral edge 422 on each of the plates such that the edge walls 424 on each plate are joined or, alternatively, one plate includes an edge wall 424 that is joined to the peripheral edge 422 of the other plate. In addition, the plates 418, 420 may be joined without an edge wall 424.

In accordance with one or more embodiments, the one of the plates 418, 420 include an inlet 414 and the other plate includes an outlet 416. In a specific embodiment, the inlet 414 formed on one of the two plates 418, 420 are formed at the same position as the outlet 416 formed on the other plate. In a more specific embodiment, the inlet 414 and outlet 416 are formed at a distance from the peripheral edge 422. In an even more specific embodiment, the inlet 414 and outlet 416 are formed at a center point of each plate measured from the peripheral edge 422.

Figure 8:
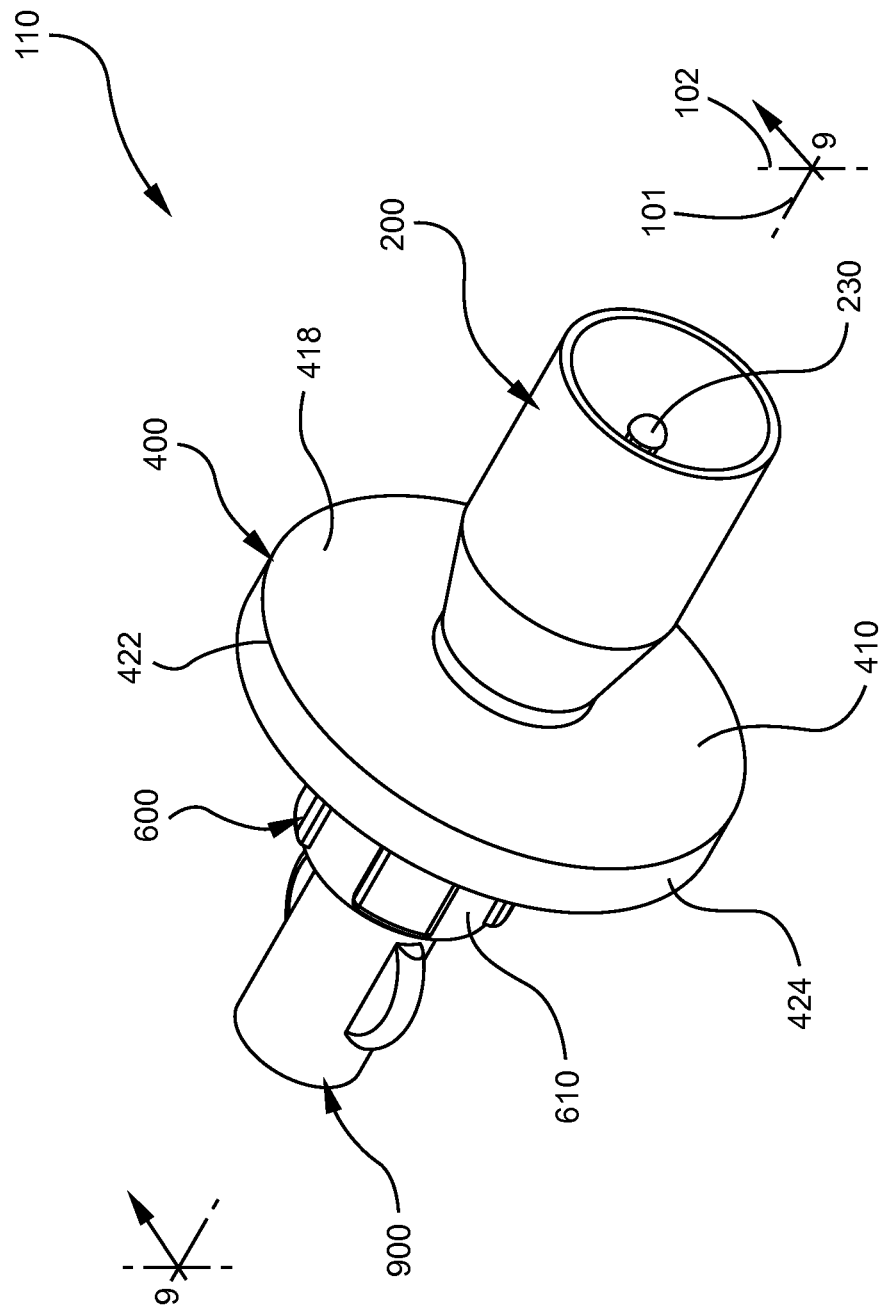
FIG. 8 illustrates a perspective view of a drug delivery system including a conduit according to one or more embodiments of the present invention.
Figure 9:
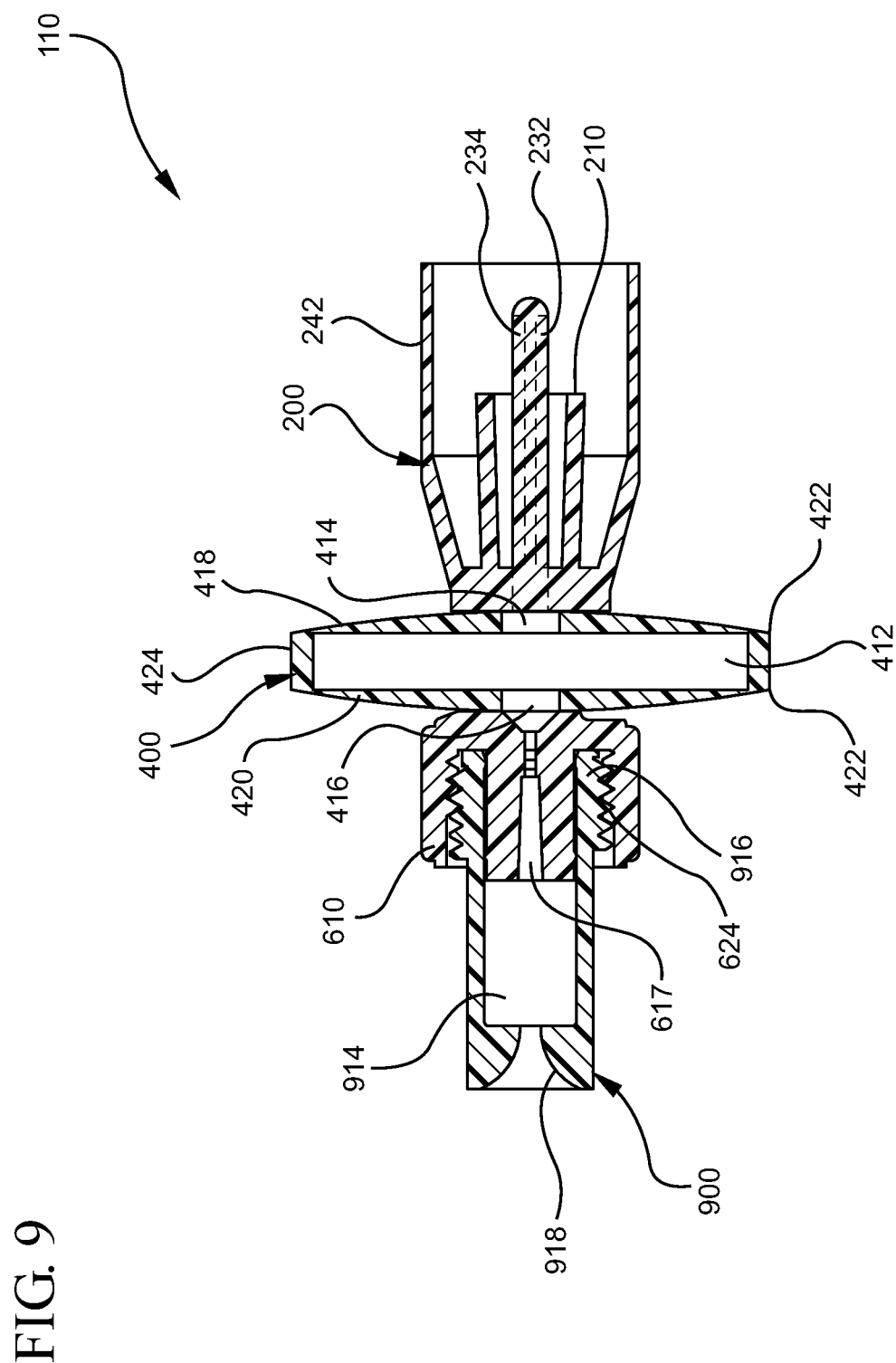
FIG. 9 shows a side cross-sectional view of the drug delivery system and conduit shown in FIG. 8 taken along line 9-9.
Figure 10:
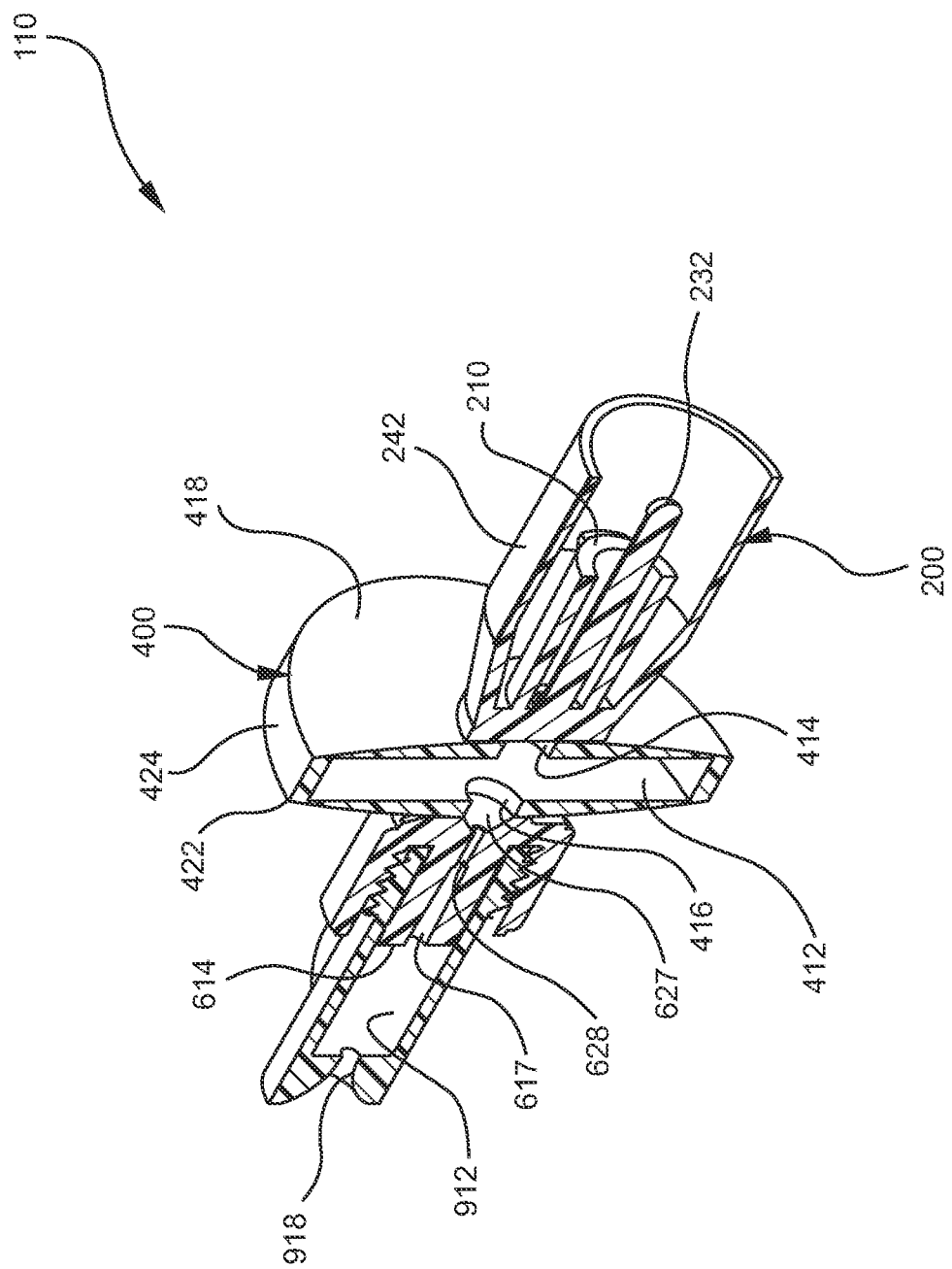
FIG. 10 illustrates a perspective view of the drug delivery system and conduit shown in FIG. 9.
Figure 11:
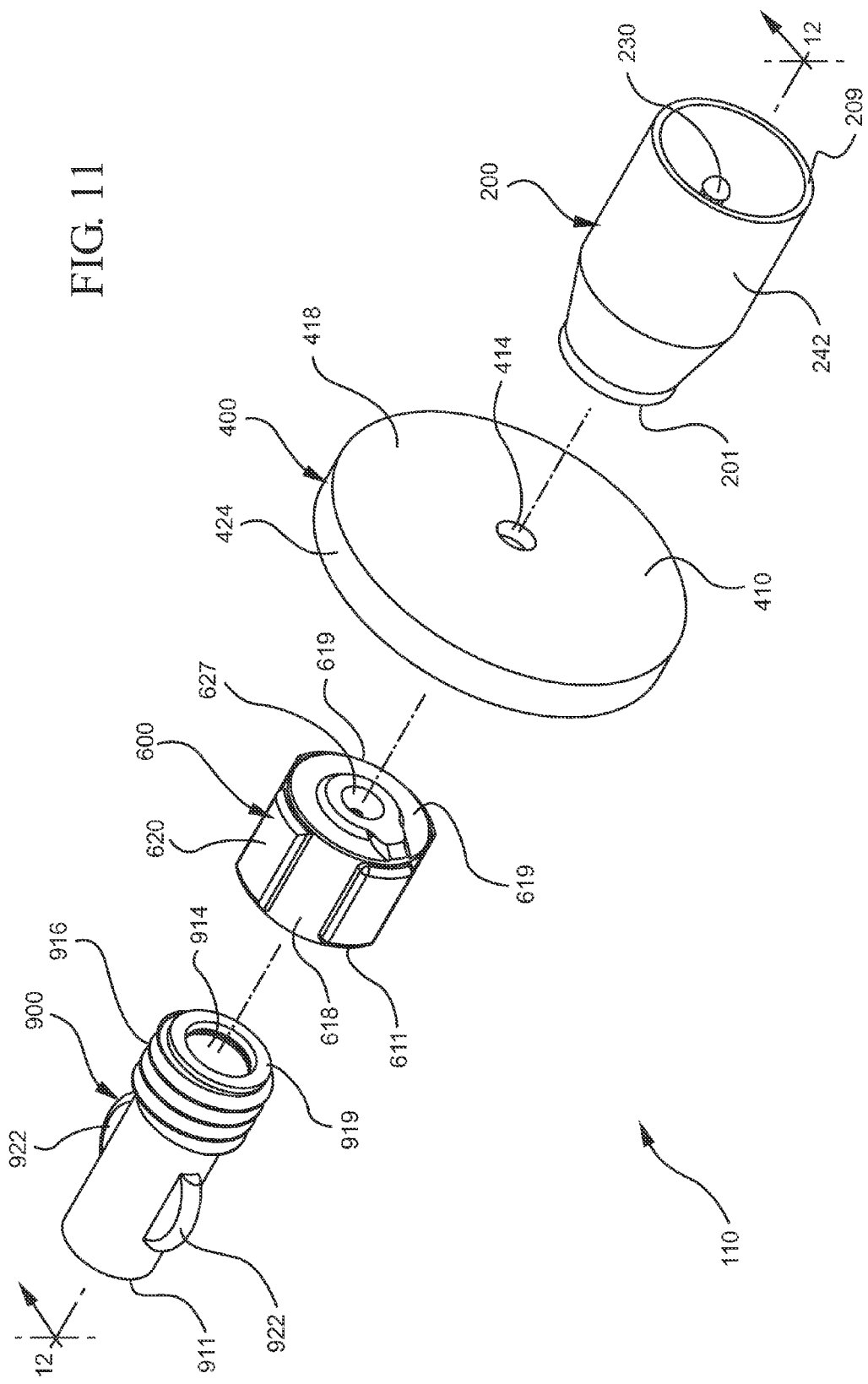
FIG. 11 shows a disassembled view of the drug delivery system shown in FIG. 8.
Figure 12:
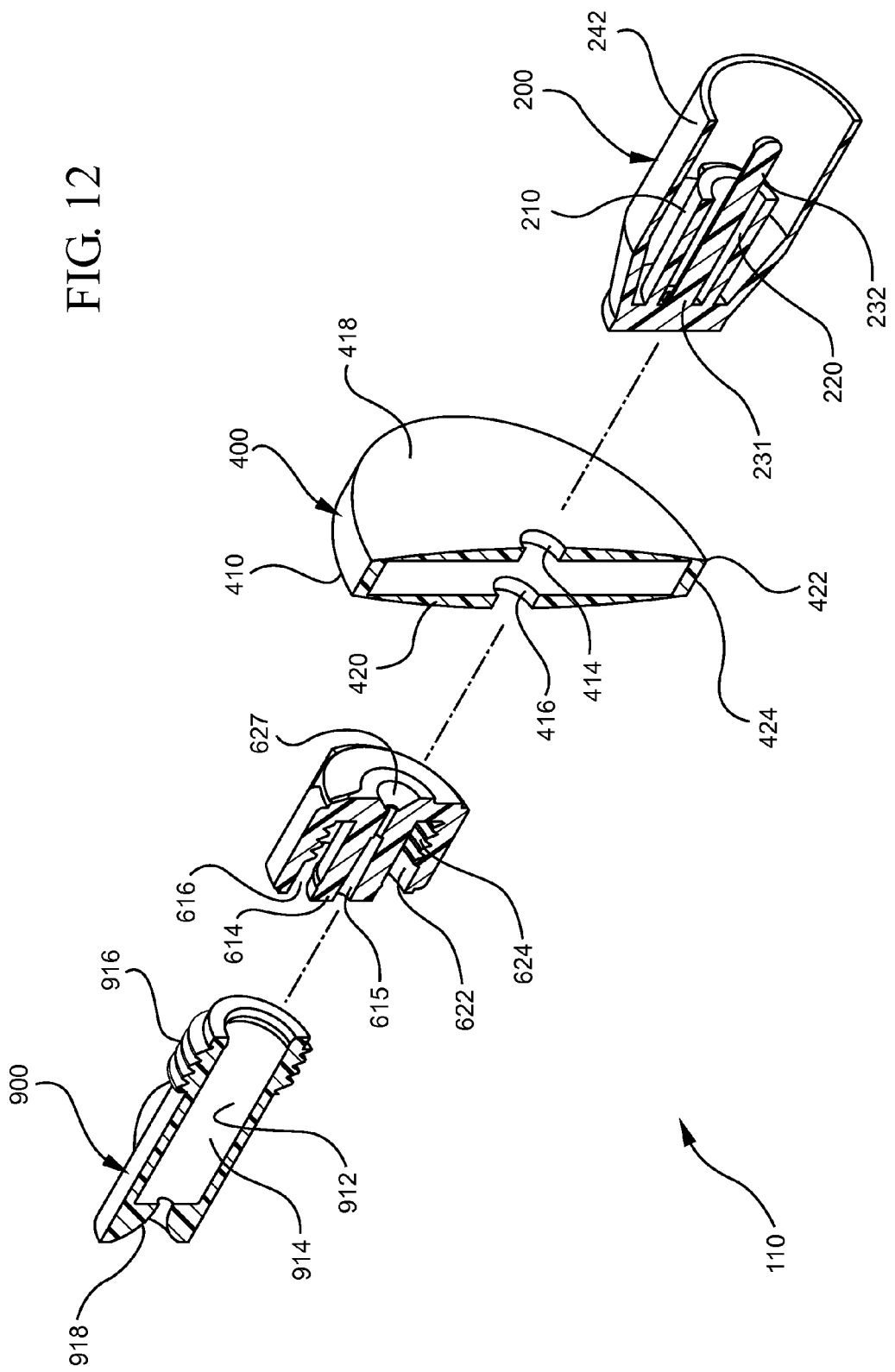
FIG. 12 illustrates a cross-sectional view of the drug delivery system and conduit shown in FIG. 11 taken along line 12-12.
Figure 13:
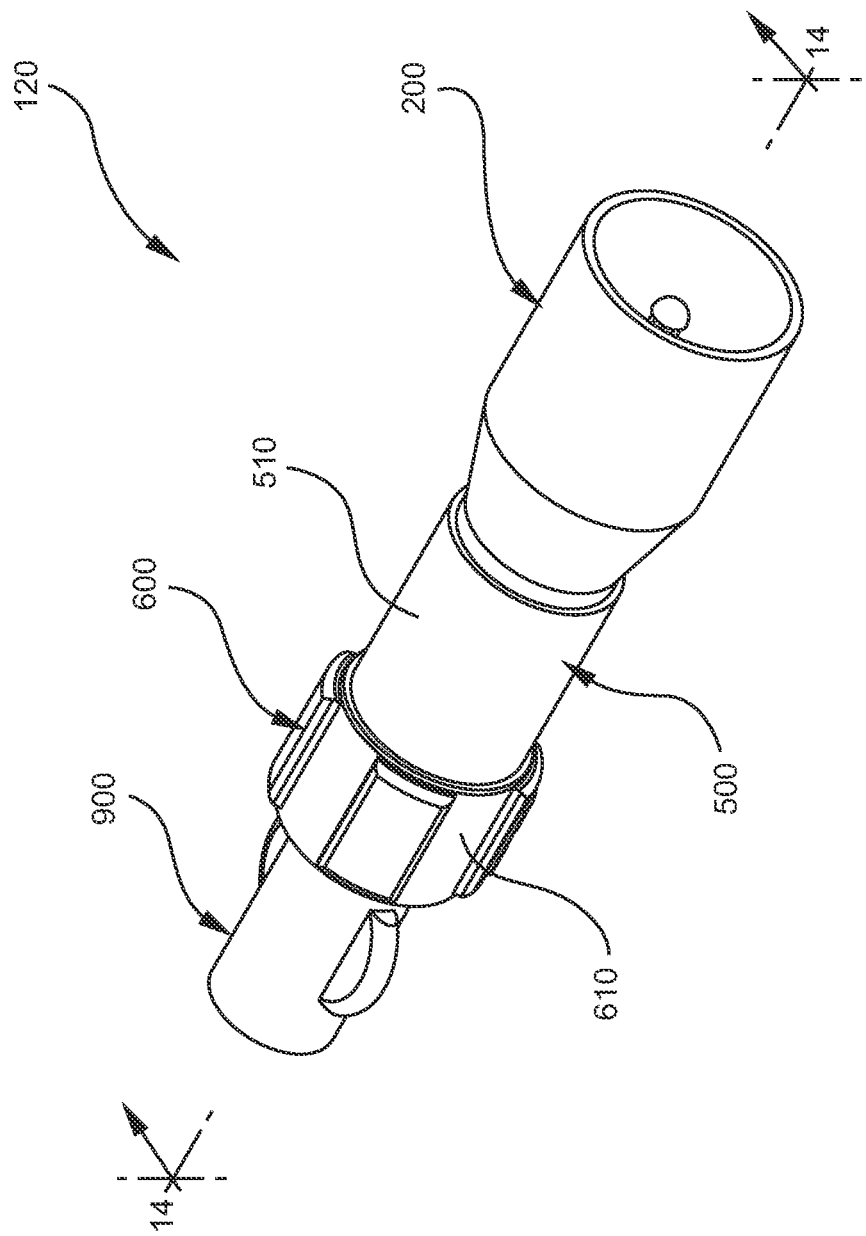
FIG. 13 illustrates a perspective view of a drug delivery system including a conduit according to one or more embodiments of the present invention.
Figure 14:
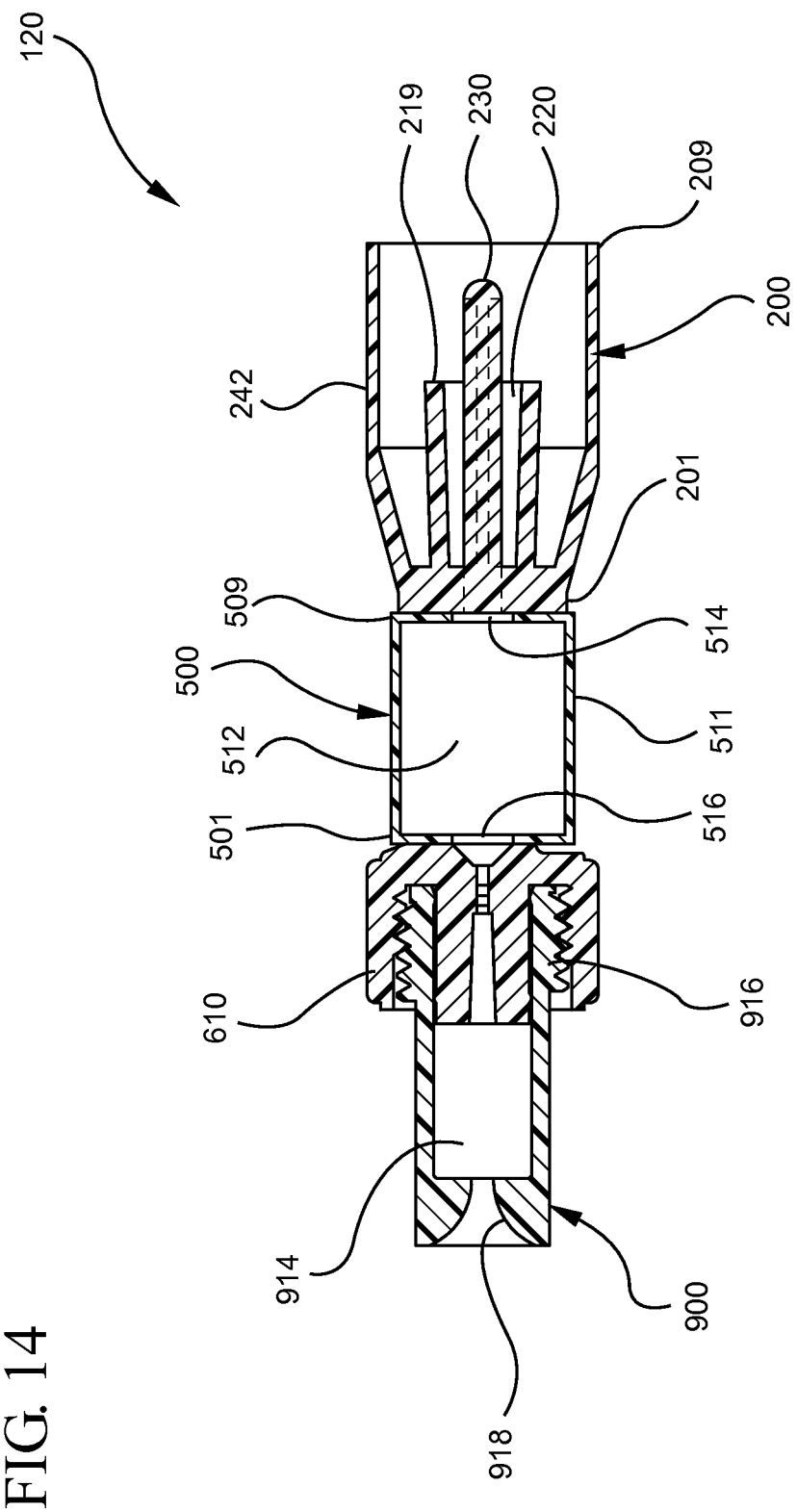
FIG. 14 shows a side cross-sectional view of the drug delivery system and conduit shown in FIG. 13 taken along line 14-14.
Figure 15:
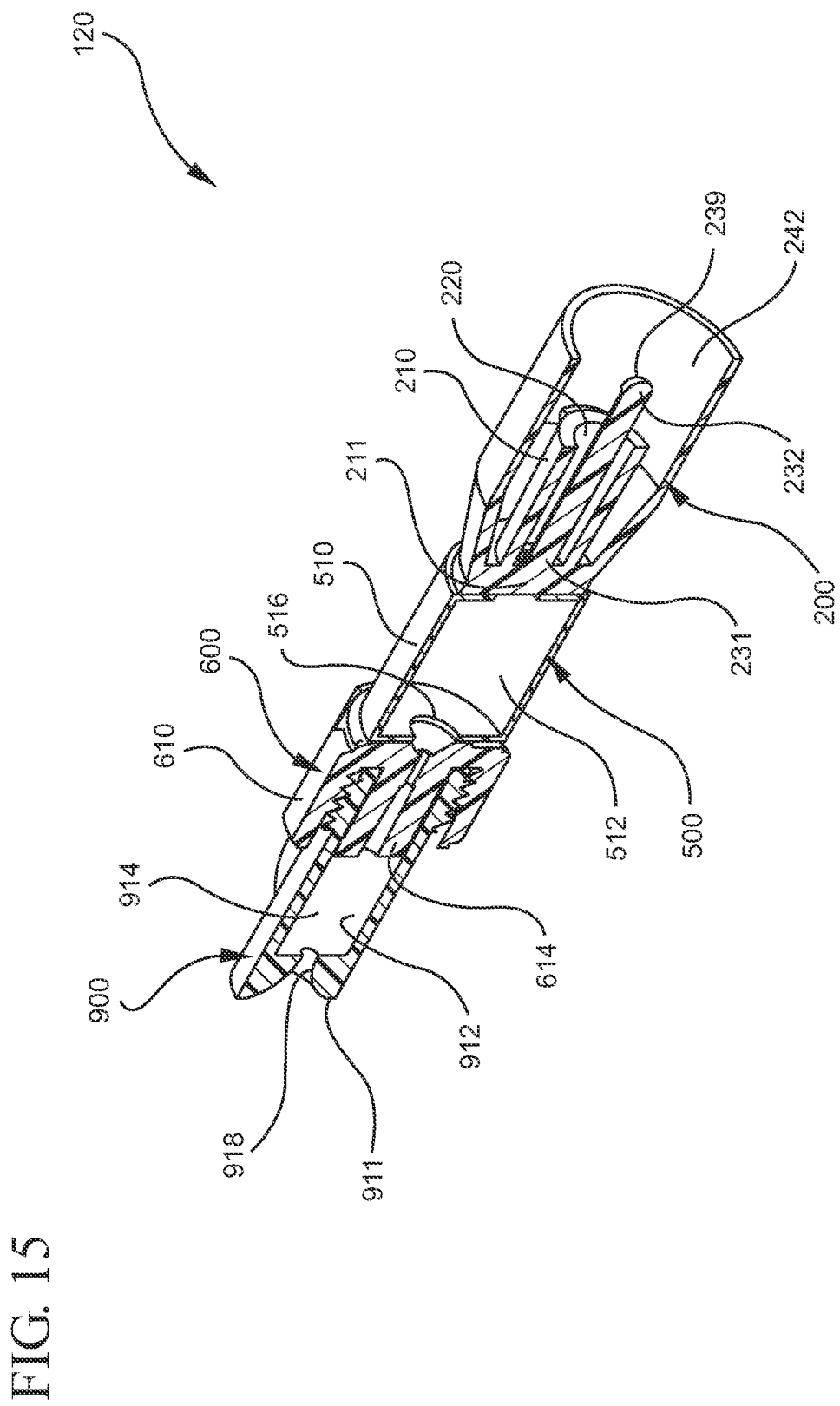
FIG. 15 illustrates a perspective view of the drug delivery system and conduit shown in FIG. 14.
Figure 16:
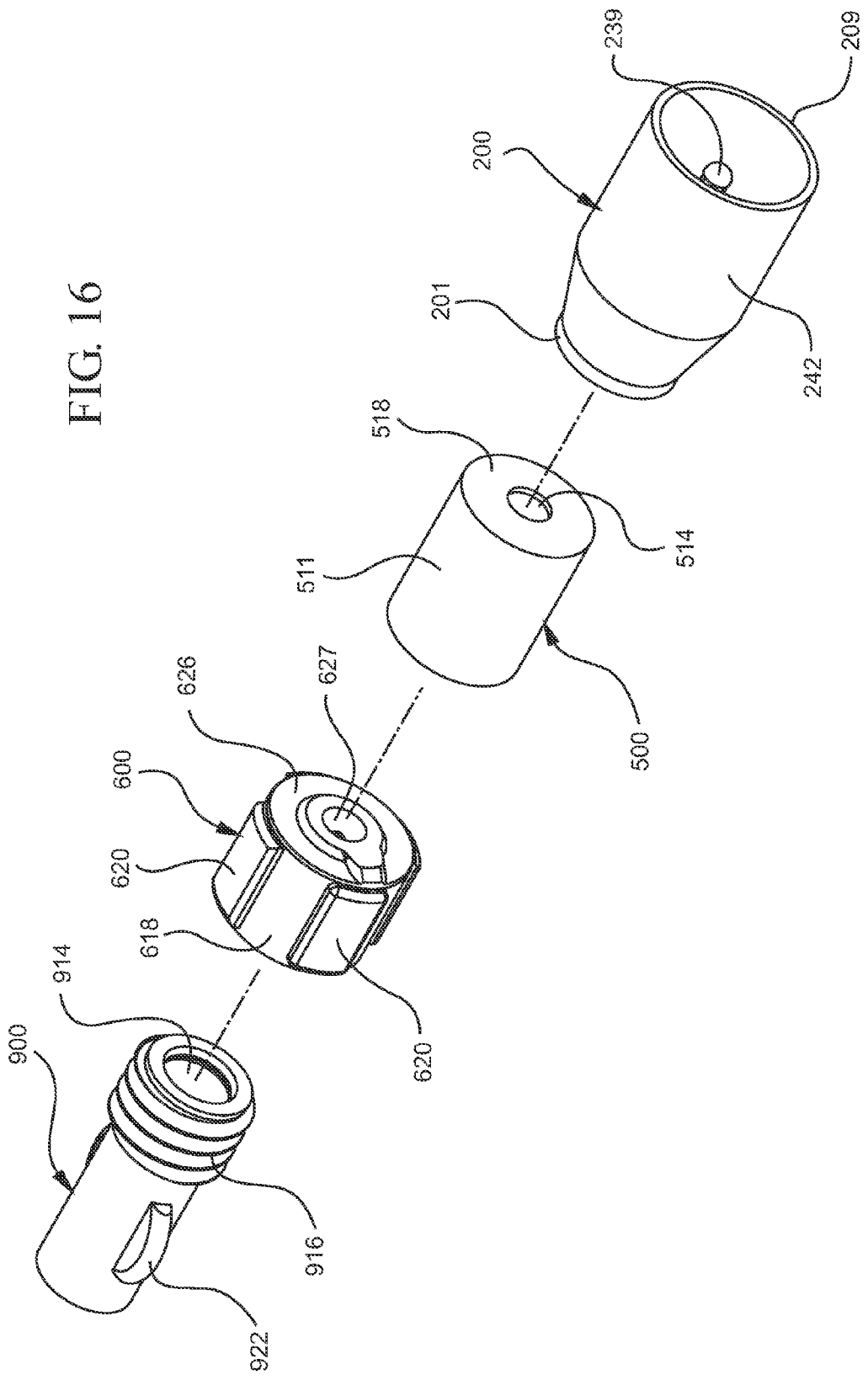
FIG. 16 shows a disassembled view of the drug delivery system shown in FIG. 13.

In one or more embodiments, the inlet 414 is formed on one of the two plates 418, 420 at a different position from the outlet 416 formed on the other plate, so the path between the inlet 414 and outlet 416 is not direct and medication must travel from the inlet 414 through indirect portions of the cavity 412 to exit through the outlet 416. In such embodiments in which the plates include an inlet 414 and outlet 416, the housing 410 may be attached to the actuator 230 with the plates 418, in a vertical alignment or in perpendicular arrangement with respect to the actuator assembly and the first axis 101 or, in other words, along the second axis 102 which is perpendicular to the first axis 101, as shown in FIG. 8. The use of a vertically aligned housing 410 reduces the space required for the attachment of the filter 400 and actuator assembly 200 to a catheter or other drug delivery site.

FIGS. 13-16 illustrate a filter 500 according to one or more embodiments. In one or more embodiments, the filter 500 includes a housing 510 that has a cylindrical shape. The filter 500 includes a distal end 501 and a proximal end 509 and the housing 510 has a hollow cylindrical body 511 extending from the distal end 501 and the proximal end 509. Proximal end 509 of the housing 510 may include an inlet 514 and the distal end 501 may include an outlet 516, both in fluid communication with a cavity 512 defined by the hollow cylindrical body 511. The proximal end 509 and/or distal end 501 may optionally include one or more duct walls 518 connecting the cylindrical body 511 and the inlet 514 and/or outlet 516. In one or more embodiments, the cylindrical body 511 is integrally molded. In an alternative embodiment, the cylindrical body may be formed from two components having a semi-circular cross-section (not shown).

In the embodiment shown in FIGS. 1-20, the cavity formed by the plates 318, 320, 418, 420 or the hollow cylindrical body 511 contains filter membranes, for removing particulate matter from the medication injected from the drug delivery connector and/or container, such as glass sharps or other foreign matter. Exemplary filter membrane materials include particles, fibers and combinations thereof. In a specific embodiment, the cavity may include a plurality of barriers for supporting and dispersing the filter membranes within the cavity. In one or more embodiments, the cavity may contain both the plurality of barriers and filter membranes.

The outlets of the housings described herein may include a conduit 600 in fluid communication with the cavities of the housings for supplying medication to a catheter or other drug delivery site. The conduit 600 may be integrally formed or permanently attached to the distal end of the filter housing. The conduit 600 may have a structure for attachment to catheters using a standard luer connection or non-luer connection. In alternative embodiments, the distal end of the filter housing may include alternative means for attaching the filter housing to a catheter or drug delivery site.

In one or more embodiments, the conduit 600 includes an angled portion (not shown) that permits the housing and actuator assembly to remain aligned along the first axis 101 and permits the connection to a catheter or other drug delivery sites that are disposed at different angles not parallel to the first axis. This angled configuration allows ease of use during attachment of the filter and actuator assembly to a catheter on the patient's body. The angled portion may define an angle between 0 degrees and 90 degrees measured from the first axis.

As shown in FIGS. 17-18, the conduit 600 may include a standard luer fitting 630 in fluid communication with the outlet 316 of the housing 310. In such embodiments, the standard luer fitting 630 includes an open distal end 631, an open proximal end 639 and a luer body 632 extending from the open distal end 631 to the open proximal end 639 in fluid communication with the outlet 316 of the housing 310. In one or more embodiments, the standard luer fitting 630 is integrally formed at the outlet 316 of the housing 310 by molding or permanently attached to the out let of the filter 300 using glue or ultrasonic welding techniques. In a specific embodiment, the standard luer fitting 630 may be attached to the outlet 316 of the housing 310 by other means known in the art. The standard luer fitting 630 may also be removably attached to the outlet 316 of the housing 310, for example, by using threaded engagement (not shown).

In one or more embodiments, the luer body 632 includes having an outside surface 634 that includes a luer lock component disposed adjacent to the open distal end 631. In a specific embodiment, the luer lock component includes at least one radially outwardly extending member that engages a threaded portion disposed on an inside surface of a corresponding luer lock fitting (not shown) on a catheter or other drug delivery site. In the embodiment shown in FIGS. 17-18, the at least one member includes two radially outwardly extending lugs 635, 636. In an even more specific embodiment, the radially outwardly extending member includes a peripheral ridge (not shown) extending around the open distal end. In one or more embodiments, the luer body includes an inside surface 637 forming a luer slip fitting. In a specific embodiment, the inside surface 637 of the luer body defines a tapered cross-sectional width that increases from the open proximal end 639 to the open distal end 631 and is adapted to engage with a corresponding luer slip fitting on a catheter or other drug delivery site.

In accordance with one or more embodiments, the conduit 600 may include an adaptor for connection to catheters having a non-luer configuration. As shown in FIGS. 1-16, the conduit 600 may include an adaptor 610 includes an open distal 611 end and an open proximal end 619 in fluid communication with the outlet of the filter housing.

The proximal end 639 of the adaptor 630 may include a connection mechanism for attachment to the filter. In one or more embodiments, the proximal end 619 of the adaptor 610 is integrally formed to the outlet of the filter by molding or other methods known in the art. In one or more alternative embodiments, the proximal end 619 of the adaptor 610 is permanently attached to the outlet of the filter using glue or ultrasonic welding or other methods known in the art.

In one or more embodiments, the adaptor 610 is a separate component that is removably attached to the outlet of the filter using a connection mechanism. FIGS. 1-16, the adaptor 610 includes a connection mechanism for attaching the adaptor to the outlet of the filter that comprises a sleeve (not shown) with internal threads (not shown). In one or more embodiments, the outlet of the housing includes corresponding structure for engaging the sleeve (not shown), for example, a distally extending threaded portion (not shown) having externally facing threads or other structure adapted to engage the internal threads (not shown) of the sleeve of the adaptor 610. In one or more embodiments, the connection mechanism for attaching the adaptor 610 to the outlet of the filter includes any connection mechanisms known in the art that provide a permanent and leak-free connection between the adaptor and the filter. In one or more alternative embodiments, such connection mechanisms may include snap fit connections or friction fit connections.

The adaptor 610 shown in FIGS. 1-16 includes an adaptor body 612 has a hollow cylindrical shape and coaxially surrounds a tubular member 614 and defining a space 616 between the adaptor body 612 and the tubular member 614. The tubular member 614 includes an inside surface 615 defining a passageway 617 in fluid communication with the filter. In the embodiment shown in FIG. 2, the passageway 617 has a cross-sectional width that decreases from the open distal end 611 to the open proximal end 619. In one or more alternative embodiments, the passageway 617 has a constant cross-sectional width. In one or more embodiments, the tubular member 614 may have a tapered cross-section or a constant cross-section. The adaptor body 612 and includes an external surface 618 having an optional grip portion to facilitate rotation of the adaptor body 612 and connection of the adaptor 610 to the outlet of the filter. In one or more embodiment, the grip portion comprises a plurality of fins 620 extending radially outwardly from the external surface 618. In a specific embodiment, the plurality of fins 620 may extend longitudinally from the distal end 611 of the adaptor to the proximal end 619 of the adaptor. The plurality of fins 620 may be equally spaced around the circumference of external surface 618 of the adaptor body 612. In one or more embodiments, the plurality of fins 620 may comprise two fins disposed diametrically or on opposite sides of the external surface 618 of the adaptor body 612. In one or more embodiments, the plurality of fins 620 may comprise three or four fins. In a specific embodiment, the grip portion may include a textured surface (not shown) or coating (not shown) disposed along the external surface 618. The adaptor body 612 includes an internal surface 622 including a threaded portion 624 for engaging a non-luer fitting, as shown in FIGS. 1-16. The open proximal end 619 may include a distal wall 626 extending from the external surface 618 to the passageway 617 defined by the tubular member 614. The distal wall 626 may further include a funnel-shaped opening 627 for facilitating fluid flow between the filter and the tubular member 614. The funnel-shaped opening 627 extends from the distal wall into the passageway 617 and has a cross-sectional width that decreases from the open proximal end 619 toward the open distal end 611. In one or more embodiments, the funnel-shaped opening 627 includes a narrowed portion 628 distally adjacent to the funnel-shaped opening 627. The narrowed portion 628 may have a smaller cross-sectional width than the funnel-shaped opening 627 and the passageway 617. In the embodiment shown in FIG. 2, the outlet 316 of the filter includes an expanded portion 317 adjacent the outlet 316 defined by a ledge 315 extending in the proximal direction from one of the plates 318, 320. The funnel-shaped opening 627 facilitates from the expanded portion 317 of the filter 300.

An exemplary non-luer fitting 900 is shown in FIGS. 1-16 and includes an open distal end 911 and an open proximal end 919. The non-luer fitting 900 includes an internal surface 912 defining a tubular chamber 914. The open proximal end 919 includes a threaded portion 916 for engaging the threaded portion 624 disposed on the internal surface 622 of the adaptor body 612. In alternative embodiments, the adaptor body 612 may have a threaded portion 624 on its external surface 618, and the non-luer fitting 900 may include a threaded portion (not shown) on its inside surface 912 for engagement with the threaded portion 624 of the adaptor body 612. In the embodiment shown, the distal end 911 of the non-luer fitting 900 includes a tubing connector 918 having a Tuohy-Borst adapter. The Tuohy-Borst adapter includes a compressible tubular or ring-shaped rubber gasket that has a central passageway longitudinally extending into the chamber to form a beveled entry on the distal end of the adaptor. In use, a catheter is fed through the opening of the rubber gasket. By compressing the rubber gasket in the longitudinal direction, the gasket will collapse and grip the catheter. Alternative connection structures may be included in the open distal end 911 of the non-luer fitting 900 that are known in the art.

In one or more embodiments, the non-luer fitting 900 has an outside surface 920 including one or more outwardly extending protrusions 922 to facilitate rotation of the non-luer fitting 900 and engagement of the non-luer fitting 900 to the adaptor body 612. In an alternative embodiment, the non-luer fitting 900 may be integrally formed or permanently attached to the outlet of the filter.

A second aspect of the present invention pertains to a method of administering epidural anesthesia to a catheter. In one or more embodiments, the method includes attaching the drug delivery systems described herein to a catheter or drug delivery site and a container and/or a drug delivery connector containing medication. In one or more embodiments the method includes providing a drug delivery system as described herein. In a specific embodiment in which the filter housing and actuator assembly do not include a connection mechanism for connecting the filter housing to a catheter or drug delivery site, the method includes attaching a standard luer fitting or non-luer fitting to the outlet of the filter housing and/or conduit. The method may include attaching a conduit to the outlet prior to attachment of the standard luer fitting or non-standard luer fitting.

FIGS. 19 and 20 illustrate one or more embodiments of the method for administering epidural anesthesia to a catheter. As shown in FIG. 19, the non-luer fitting 900 is attached to the adaptor 610, which is attached to the outlet 516 of filter 500. The container is shown as syringe 800 attached to a drug delivery connector 700 that includes a valve 724 for preventing fluid communication between the cavity 722 and the open distal end 711. In one or more embodiments of the method may be utilized with a container and/or drug delivery connector that are free of valves.

In the embodiment shown, the method includes attaching the drug delivery system to a delivery site, which may include a catheter 1000. In one or more embodiments, the method includes attaching the drug delivery system to a container containing a medication by attaching the hub 210 of the actuator assembly 200 to the container. In the embodiment shown, the drug delivery system 120 includes a cylindrically shaped filter 500 and the container is shown in the form of a syringe 800 including a plunger rod 840 as described herein, and includes a drug delivery connector 700 attached to the tip 820 of the syringe barrel 810 and such that the cavity 722 of the drug delivery connector 700 is in fluid communication with the chamber 818 of the syringe barrel 810.

In one or more embodiments, attaching the drug delivery system 120 to the container includes inserting the projection 232 of the actuator assembly 200 into the open distal 711 end of the drug delivery connector 700 and securing engagement of the hub 210 to the open distal end 711 of the drug delivery connector 700. In embodiments which utilizes a container and/or drug delivery connector having a luer slip tip, securing engagement of the hub 210 and the open distal end 711 of the drug delivery connector includes applying a force to the container and/or drug delivery connector in the distal direction so the projection enters the opening of the container, or in the embodiment shown, the open distal end 711, of the drug delivery connector until the open distal end 711 engages the inside surface 215 of the hub 210. The method further includes continuing to apply a force in the distal direction until the inside surface 215 of the hub 210 is connected to the container and/or drug delivery connector in a friction fit engagement. In embodiments which utilize a container and/or drug delivery connector having a luer lock fitting, the method includes applying a force to the container and/or drug delivery connector in the distal direction so the projection 232 extends into the opening of the container and/or drug delivery connector and the luer lock structure 216 at the proximal end 219 of the hub 210 engages the luer lock fitting. In the embodiment shown, the open distal end 711 of the drug delivery connector 700 includes a tip 712 and a threaded collar 714 and the method includes inserting the projection 232 into the tip 712 and rotating the container and/or drug delivery connector such that the tabs 217, 218 to engage the threaded collar 714.

As the drug delivery system is connected to the container and/or drug delivery container, the projection enters the container or drug delivery connector and exerts a force on the one-way valve and opens the valve to permit fluid flow between the container and/or drug delivery container and the drug delivery system. The aspirated medication exerts a force on the one-way valve to close the valve. The closed valve prevents the medication from leaking out of the syringe barrel 810 prior to attachment to the drug delivery system. As the drug delivery system is connected to the container and/or drug delivery container, the projection enters the container or drug delivery connector and exerts a force on the one-way valve and opens the valve to permit fluid flow between the open distal end 711 and the cavity 722.

In one or more embodiments, the method of administering epidural anesthesia utilizes a container in the form of a syringe including a valve and plunger rod assembly (not shown) and no drug delivery connector. In such embodiments, projection is inserted into the open tip of the syringe and the hub is secured to the syringe barrel. Similarly, the method for administering epidural anesthesia described herein may be utilized with syringes with no valves. In such embodiments, the projection would be inserted into the tip and the hub would be secured to the syringe barrel.

In one or more embodiments, the method includes applying a force to the plunger rod 840 in the distal direction to expel the medication contained within the syringe barrel 810 into the drug delivery connector 700 and through the open distal end 711, which is now in fluid communication with the cavity 722. Engagement of the hub 210 to the open distal end 711 permits the medication to flow from the open distal end 711 to the openings 234 of the projection 232 and through the filter 500 to a catheter 1000, as shown in FIG. 20.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A drug delivery system comprising:
    an actuator assembly including a distal end, a proximal end, a projection including one or more openings extending the length of the projection, the projection attached at the distal end of the actuator assembly and extending in a proximal direction from the distal end of the actuator assembly, a hub including a base having a plurality of inlets, the plurality of inlets being in fluid communication with the one or more openings of the projection, said hub attached to the distal end of the actuator assembly and disposed in a coaxial relationship with the projection, and a filter including an inlet that is integrally molded to the actuator assembly and an outlet in fluid communication with the inlet and the opening, the filter comprises a housing attached to the actuator assembly in a vertical alignment with respect to the actuator assembly; and
    a conduit attached to the outlet of the filter for attachment of the drug delivery system to a delivery site.

2. The drug delivery system of claim 1, wherein the inlet of the filter is formed at a different position from the outlet of the filter such that a path between the inlet and outlet is not direct.

3. The drug delivery system of claim 1, wherein the hub includes an open proximal end for receiving an open end of a container.

4. The drug delivery system of claim 1, wherein the conduit comprises a luer fitting.

5. The drug delivery system of claim 1, wherein the conduit comprises an adaptor for securing a non-luer fitting to the outlet.

6. The drug delivery system of claim 1, wherein the opening of the projection comprises two intersecting beams extending from the distal end to the proximal end of the actuator assembly.

7. The drug delivery system of claim 1, wherein the hub comprises a luer lock structure for engaging a container comprising a luer lock fitting.

8. The drug delivery system of claim 1, further comprising a shield attached to the distal end of the actuator assembly and surrounding the hub in a coaxial relationship.

9. The drug delivery system of claim 1, wherein the housing includes a cavity comprising filter material.

10. The drug delivery system of claim 9, wherein the housing comprises a top plate and a bottom plate welded together.

11. The drug delivery system of claim 9, wherein the housing comprises a cylindrical body.

12. A method of administering medication to a delivery site comprising:
    providing a drug delivery system comprising an actuator assembly having a proximal end and a distal end that is integrally molded to an inlet of a filter, the filter comprising an outlet in fluid communication with the inlet; the filter comprises a housing attached to the actuator assembly in a vertical alignment with respect to the actuator assembly and the actuator assembly including a projection with one or more openings extending the length of the projection, the one or more openings extending from the distal end in a proximal direction, the opening in fluid communication with the outlet of the filter;
    attaching the outlet of the filter to a delivery site; and
    attaching an open end of a container including a medication to the actuator assembly.

13. The method of claim 12, wherein the actuator assembly comprises a hub including a base having a plurality of inlets, the plurality of inlets being in fluid communication with the one or more openings of the projection, said hub attached to the distal end of the actuator assembly and extending in the proximal direction in a coaxial relationship with the projection and attaching the open end of a container comprises inserting the projection into the open end and securing the hub to the open end of the container.

14. The method of claim 12, wherein the container comprises one of a syringe barrel and a drug delivery connector and the medication comprises epidural anesthesia.

15. The method of claim 14, wherein the container comprises a one-way valve for preventing fluid communication between the open end of the container and the opening of the projection.

16. The method of claim 15, wherein the delivery site comprises an epidural catheter.

* * * * *